United States Patent
Tsai et al.

(10) Patent No.: US 12,338,214 B2
(45) Date of Patent: Jun. 24, 2025

(54) BEXAROTENE DERIVATIVES AND THEIR USE IN TREATING CANCER

(71) Applicant: DJ THERAPEUTICS LLC, Long Beach, CA (US)

(72) Inventors: Donald Tsai, Los Angeles, CA (US); David Kaelin, Los Angeles, CA (US)

(73) Assignee: DJ Therapeutics LLC, Long Beach, CA (US)

(*) Notice: Subject to any disclaimer, the term of this patent is extended or adjusted under 35 U.S.C. 154(b) by 1066 days.

(21) Appl. No.: 16/971,736

(22) PCT Filed: Mar. 1, 2019

(86) PCT No.: PCT/US2019/020298
§ 371 (c)(1),
(2) Date: Aug. 21, 2020

(87) PCT Pub. No.: WO2019/169270
PCT Pub. Date: Sep. 6, 2019

(65) Prior Publication Data
US 2021/0363093 A1    Nov. 25, 2021

Related U.S. Application Data

(60) Provisional application No. 62/637,387, filed on Mar. 1, 2018.

(51) Int. Cl.
| | | |
|---|---|---|
| *C07C 63/66* | (2006.01) | |
| *A61P 35/00* | (2006.01) | |
| *C07C 63/49* | (2006.01) | |

(52) U.S. Cl.
CPC .............. *C07C 63/66* (2013.01); *A61P 35/00* (2018.01); *C07C 63/49* (2013.01); *C07C 2602/10* (2017.05)

(58) Field of Classification Search
CPC ..... C07C 63/66; C07C 63/49; C07C 2602/10; C07C 63/74; C07C 13/48; A61P 35/00; A61P 17/06; A61P 5/14; A61P 17/00; A61P 35/02; A61K 31/192
See application file for complete search history.

(56) References Cited

U.S. PATENT DOCUMENTS

| | | |
|---|---|---|
| 5,962,731 A | 10/1999 | Boehm et al. |
| 2004/0019072 A1 | 1/2004 | Canan-Koch et al. |
| 2004/0198980 A1 | 7/2004 | Haffner et al. |
| 2013/0225594 A1 | 8/2013 | Craighead et al. |
| 2014/0235676 A1 | 8/2014 | Landreth |

FOREIGN PATENT DOCUMENTS

| | | |
|---|---|---|
| JP | H08-505852 A | 6/1996 |
| JP | 2002-515025 A | 5/2002 |
| JP | 2014528486 A | 10/2014 |
| WO | 9321146 | 10/1993 |
| WO | 94/15901 A1 | 7/1994 |
| WO | 9415902 A1 | 7/1994 |
| WO | 97/12853 | 4/1997 |
| WO | 2011103321 A1 | 8/2011 |

OTHER PUBLICATIONS

Patani, G. A. et al. "Bioisosterism: A Rational Approach in Drug Design." Chemical reviews 1996, vol. 96, 8: 3147-3176. (Year: 1996).*
Aiguo Dong et al., 3D-Pharmacophore Model for RXR, Agonists, Neurochemistry International, vol. 54, 2009, pp. 286-291.
Office Action of EA202091802 dated Oct. 21, 2021.
Sigrid E. Berg et al., Successful Treatment of Relapsed Lymphomatoid Granulomatosis With Bexarotene, Cancer Biology & Therapy, Oct. 1, 2008, vol. 7:10, pp. 1544-1546.
Marcus F. Boehm et al., Synthesis and Structure-Activity Relationships of Novel Retinoid X Receptor-Selective Retinoids, J. Med. Chem. 1994, vol. 37, pp. 2930-2941.
Marcus F. Boehm et al., Design and Synthesis of Potent Retinoid X Receptor Selective Ligands That Induce Apoptosis in Leukemia Cells, J. Med. Chem. 1995, vol. 38, pp. 3146-3155.
Madeleine Duvic et al., Bexarotene is Effective and Safe for Treatment of Refractory Advanced Stage Cutaneous T-Cell Lymphoma: Multinational Phase II-III Trial Results, Journal of Clinical Oncology, May 1, 2001, vol. 19, No. 19, pp. 2456-2471.
Francisco J. Esteva et al., Multicenter Phase II Study of Oral Bexarotene for Patients With Metastatic Breast Cancer, Journal of Clinical Oncology, Mar. 15, 2003, vol. 21, No. 6, pp. 999-1006.

(Continued)

*Primary Examiner* — Jean P Cornet
*Assistant Examiner* — Chihyi Lee
(74) *Attorney, Agent, or Firm* — McAndrews, Held & Malloy, Ltd.

(57) ABSTRACT

Compounds of the invention, such as compounds of formula (I):

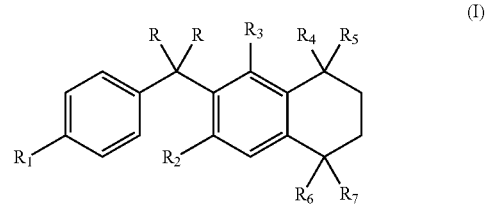

where R, $R_1$, $R_2$, $R_3$, $R_4$, $R_5$, $R_6$, and $R_7$ are defined herein, are useful for treating cancer, autoimmune disorders, and/or skin dermatitis, and/or methods for increasing peripheral blood counts and/or improving immune system function. Pharmaceutical compositions containing the compounds and methods of using the compounds are also disclosed.

24 Claims, 5 Drawing Sheets

(56) References Cited

OTHER PUBLICATIONS

International Preliminary Report on Patentability, PCT/US2019/020298, dated Sep. 1, 2020.
Suzan McNamara et al., Expanding the Use of Retinoids in Acute Myleoid Leukemia: Spotlight on Bexarotene, Clinical Cancer Research, 2008, vol. 14(17), Sep. 1, 2008.
Eun-Jung Park et al., Induction of Retinoid X Receptor Activity and Consequent Up-Regulation of 21WFF1/CIIP1 by Indenoisoquinolines in MCF7 Cells, Cancer Prev. Res. (Phila), Apr. 2011, vol. 4, pp. 592-607.
PV Sanchez et al., Induced Differentiation of Acute Myeloid Leukemia Cells by Activation of Retinoid X and Liver X Receptors, Leukemia, 2014, vol. 28, pp. 749-760.
Donald E. Tsai et al., Evidence of Myeloid Differentiation in Non-M3 Acute Myeloid Leukemia Treated With the Retinoid X Receptor Agonist Bexarotene, Cancer Biology & Therapy, Jan. 2007, vol. 6:1, pp. 18-21.
Donald E. Tsai et al., A Phase I Study of Bexarotene, a Retinoic X Receptor Agonist in Non-M3 Acute Myeloid Leukemia, Clinical Cancer Research, 2008, vol. 14, pp. 5619-5625.
Donald E. Tsai et al., Successful Treatment on Angioimmunoblastic T-Cell Lymphoma With the Retinoid X Receptor Agonist, Bexarotene, Leukemia & Lympohoma, Sep. 2011, vol. 52:9, pp. 1815-1817.
Qing; Fan, A Suzuki Coupling Approach Trifluoromethyl Derivative of Targretin (LGD 1069), Bioorg. Med. Chem. Lett., vol. 7, No. 16, Aug. 19, 1997, pp. 2117-2120.
Cavasotto et al., Determinants of Retinoid X Receptor Transcriptional Antagonism, J. Med. Chem., vol. 47, No. 18, Aug. 2004, pp. 4360-4372.
Yu et al., Structural Modifications of 6-naphthalene-2-carboxylate Retinoids, Bioorganic & Medicinal Chemistry Letters, 1996, vol. 6, pp. 2865-2870.
The International Search Report (ISR) with Written Opinion for PCT/US2019/020298 dated May 7, 2019, pp. 1-10.
Pubchem CID 9799442, pp. 1-9, Create Date: Oct. 25, 2006; p. 2.
Pubchem CID 129671708, pp. 1-6, Create Date: Sep. 13, 2017; p. 2.

* cited by examiner

BEXAROTENE DERIVATIVES AND THEIR USE IN TREATING CANCER

CROSS-REFERENCE TO RELATED APPLICATIONS

This application is a U.S. national phase of International Application No. PCT/US2019/020298, filed on Mar. 1, 2019, which claims priority to U.S. Provisional Application No. 62/637,387, filed Mar. 1, 2018, both of which are incorporated by reference herein in their entirety.

BACKGROUND OF DISCLOSURE

Field of Disclosure

This disclosure relates to compositions and methods for treating cancer. Specifically, this disclosure relates to bexarotene derivatives, methods for treating cancer, autoimmune disorders, and/or skin dermatitis, and methods for increasing peripheral blood counts and/or improving immune system function.

Technical Background

Cancer is the abnormal or uncontrolled growth of cells that often leads to tumor formation, metastasis of cancerous cells from one location to another, and death of an afflicted individual. Each year, more than a dozen million new cases are diagnosed worldwide. In addition, almost 10 million cancer related deaths occur yearly worldwide. Despite significant advances in understanding and efforts to cure cancer, it is expected that the number of cancer cases per year will nearly double within the next two decades.

The primary modes of treatment for cancer include surgery, chemotherapy, radiation therapy, targeted therapy, and immunotherapy. Each of these approaches to treat cancer is effective to some degree depending upon the type of cancer, and indeed, in some instances individuals can reach full remission, where there are no signs of cancer. However, all currently available cancer treatments have limitations and none is effective once a cancer progresses or evolves to become refractory or treatment-resistant.

There is a need for new treatment regimens that are more effective against cancer, and other diseases.

SUMMARY OF THE DISCLOSURE

The disclosure provides novel compounds useful for treating cancer, autoimmune disorders, and/or skin dermatitis, or useful for increasing peripheral blood counts and/or improving immune system function. Thus, one aspect of the disclosure provides a compound of formula (I):

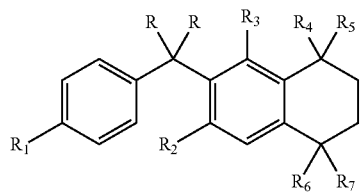
(I)

or pharmaceutically acceptable salts, esters, amides, and prodrugs thereof, wherein two R groups and the carbon atom to which they are attached form $=CH_2$ or cyclopropyl ring;

$R_1$ is selected from the group consisting of $-CO_2H$, $-CO_2(C_1-C_6$ alkyl), $-CO_2(arylC_1-C_6$ alkyl), $-CO_2$(aryl), $-CHO$, $-CONH_2$, $-CONH(C_1-C_6$ alkyl), $-CON(C_1-C_6$ alkyl$)_2$, $-CONH-OH$, $-CONH-OCO(C_1-C_6$ alkyl), $-CONH-NH_2$, $-N(R_9)SO_2R_9$, $-SO_2N(R_9)_2$, $-N(CO)NHSO_2CH_3$, tetrazole, isoxazole, hydroxyisoxazole, and oxazolidinedione;

each $R_9$ is independently selected from the group consisting of hydrogen, $C_1-C_6$ alkyl, aryl, and heteroaryl;

$R_2$ is halogen, $C_1-C_6$ alkyl, $C_1-C_6$ haloalkyl, hydroxy ($C_1-C_6$ alkyl), alkoxy ($C_1-C_6$ alkyl), amino ($C_1-C_6$ alkyl), or $-CN$;

$R_3$ is hydrogen, halogen, $C_1-C_6$ alkyl, or $C_1-C_6$ haloalkyl;

$R_4$ and $R_5$ are independently $C_1-C_6$ alkyl or $C_1-C_6$ haloalkyl, or $R_4$ and $R_5$ are together with the carbon atoms to which they are attached form $C_3-C_6$ cycloalkyl optionally substituted with one or more $R_8$;

$R_6$ and $R_7$ are independently $C_1-C_6$ alkyl or $C_1-C_6$ haloalkyl, or $R_6$ and $R_7$ are together with the carbon atoms to which they are attached form $C_3-C_6$ cycloalkyl optionally substituted with one or more $R_8$;

wherein each $R_8$ is independently selected from the group consisting of halogen, $-NO_2$, $-CN$, $C_1-C_6$ alkyl, $C_1-C_6$ haloalkyl, $-NH_2$, $-NH(C_1-C_6$ alkyl), $-N(C_1-C_6$ alkyl$)_2$, $-OH$, $C_1-C_6$ alkoxy, and $C_1-C_6$ haloalkoxy;

provided that when each of $R_2$, $R_4$, $R_5$, $R_6$, and $R_7$ are independently methyl, then $R_3$ is not hydrogen.

Another aspect of the disclosure provides a compound of formulae (II-1) to (II-6):

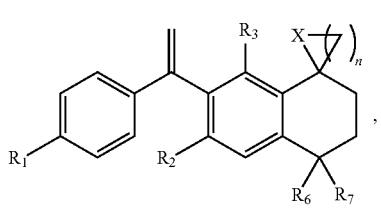
(II-1)

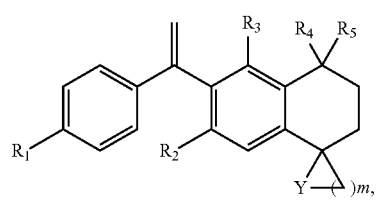
(II-2)

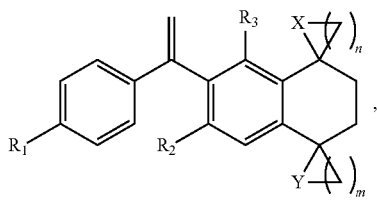
(II-3)

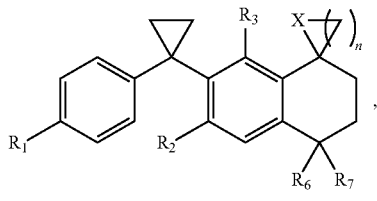
(II-4)

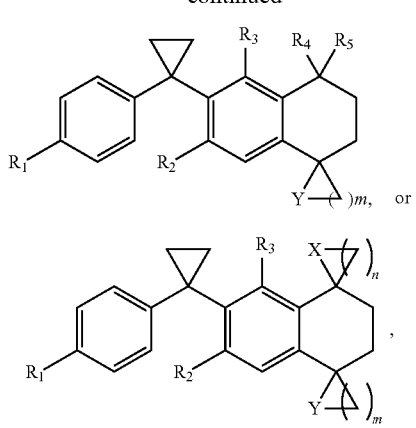

or pharmaceutically acceptable salts, esters, amides, and prodrugs thereof, wherein X is $CH_2$, O, or NH;
y is $CH_2$, O, or NH;
m is an integer 1 to 4;
n is an integer 1 to 4;
$R_1$ is selected from the group consisting of $—CO_2H$, $—CO_2(C_1$-$C_6$ alkyl), $—CO_2(arylC_1$-$C_6$ alkyl), $—CO_2$ (aryl), —CHO, $—CONH_2$, $—CONH(C_1$-$C_6$ alkyl), $—CON(C_1$-$C_6$ alkyl$)_2$, —CONH—OH, —CONH—$OCO(C_1$-$C_6$ alkyl), —CONH—$NH_2$, $—N(R_9)SO_2R_9$, $—SO_2N(R_9)_2$, $—N(CO)NHSO_2CH_3$, tetrazole, isoxazole, hydroxyisoxazole, and oxazolidinedione;
  each $R_9$ is independently selected from the group consisting of hydrogen, $C_1$-$C_6$ alkyl, aryl, and heteroaryl;
$R_2$ is halogen, $C_1$-$C_6$ alkyl, $C_1$-$C_6$ haloalkyl, hydroxy ($C_1$-$C_6$ alkyl), alkoxy ($C_1$-$C_6$ alkyl), amino ($C_1$-$C_6$ alkyl), or —CN;
$R_3$ is hydrogen, halogen, $C_1$-$C_6$ alkyl, or $C_1$-$C_6$ haloalkyl;
$R_4$ and $R_5$ are independently $C_1$-$C_6$ alkyl or $C_1$-$C_6$ haloalkyl, or $R_4$ and $R_5$ are together with the carbon atoms to which they are attached form $C_3$-$C_6$ cycloalkyl optionally substituted with one or more $R_8$;
$R_6$ and $R_7$ are independently $C_1$-$C_6$ alkyl or $C_1$-$C_6$ haloalkyl, or $R_6$ and $R_7$ are together with the carbon atoms to which they are attached form $C_3$-$C_6$ cycloalkyl optionally substituted with one or more $R_8$;
wherein each $R_8$ is independently selected from the group consisting of halogen, $—NO_2$, —CN, $C_1$-$C_6$ alkyl, $C_1$-$C_6$ haloalkyl, $—NH_2$, $—NH(C_1$-$C_6$ alkyl), $—N(C_1$-$C_6$ alkyl$)_2$, —OH, $C_1$-$C_6$ alkoxy, and $C_1$-$C_6$ haloalkoxy.

Another aspect of the disclosure provides a pharmaceutical composition including one or more compounds of the disclosure as described herein (e.g., compounds of formula (I), (I-1), (I-2), (II-1) to (II-6)) and a pharmaceutically acceptable carrier, solvent, adjuvant or diluent.

Another aspect of the disclosure provides methods for using the compounds of the disclosure. Thus, in one aspect, the disclosure provides methods for treating cancer. Such methods include administering to a subject in need thereof an effective amount of the compound of the disclosure as described herein or the pharmaceutical composition of the disclosure as described herein.

In certain embodiments, the cancer includes lymphomas (such as B and T cell non-Hodgkins lymphoma, Hodgkin lymphoma, cutaneous T cell lymphoma and all other types) and leukemia (such as Acute myeloid leukemia (AML), Acute lymphoblastic leukemia (ALL), chronic lymphocytic leukemia (CLL) and Chronic myelogenous leukemia (CML)).

One aspect of the disclosure provides methods for treating autoimmune disorders. Such methods include administering to a subject in need thereof an effective amount of the compound of the disclosure as described herein or the pharmaceutical composition of the disclosure as described herein.

Another aspect of the disclosure provides methods for treating skin dermatitis. Such methods include administering to a subject in need thereof an effective amount of the compound of the disclosure as described herein or the pharmaceutical composition of the disclosure as described herein.

Another aspect of the disclosure provides methods for increasing peripheral blood counts and/or improving immune system function. Such methods include administering to a subject in need thereof an effective amount of the compound of the disclosure as described herein or the pharmaceutical composition of the disclosure as described herein.

BRIEF DESCRIPTION OF THE DRAWINGS

The accompanying drawings are included to provide a further understanding of the methods and materials of the disclosure, and are incorporated in and constitute a part of this specification. The drawings illustrate one or more embodiment(s) of the disclosure and, together with the description, serve to explain the principles and operation of the disclosure.

DETAILED DESCRIPTION OF THE DISCLOSURE

Figure 1:
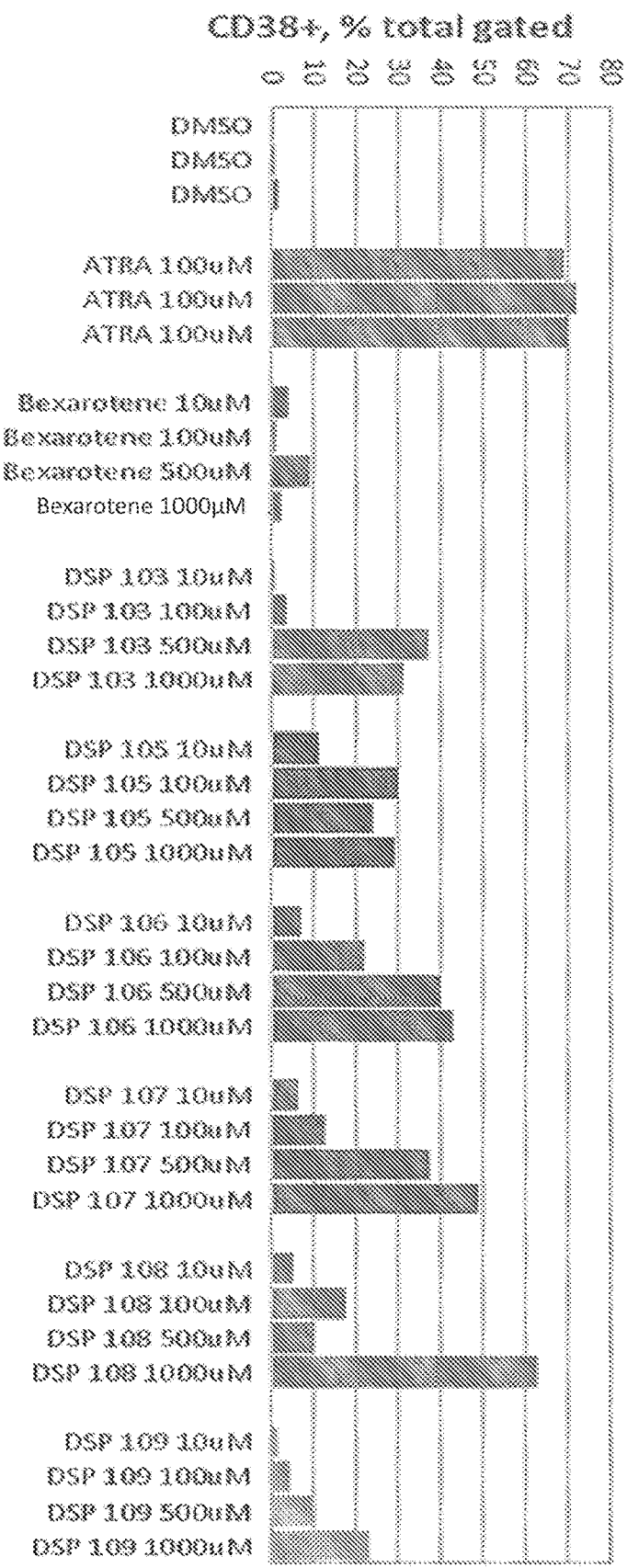
FIG. 1 illustrates the activity of the compounds of the disclosure in dose dependent CD38 expression in HL60 (human acute promyelocytic leukemia) cells.

Before the disclosed methods and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials and methods provide improvements in treatment of cancer, autoimmune disorders, and/or skin dermatitis. The disclosed materials and methods also provide improvements in immune system function and/or peripheral blood counts.

Accordingly, one aspect of the disclosure provides compounds of formula (I):

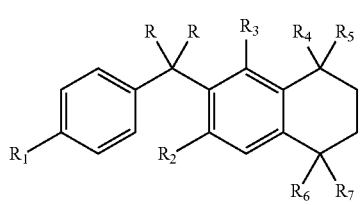

(I)

or pharmaceutically acceptable salts, esters, amides, and prodrugs thereof, wherein
two R groups and the carbon atom to which they are attached form =$CH_2$ or cyclopropyl ring;
$R_1$ is selected from the group consisting of —$CO_2H$, —$CO_2(C_1$-$C_6$ alkyl), —$CO_2$(aryl$C_1$-$C_6$ alkyl), —$CO_2$(aryl), —CHO, —$CONH_2$, —CONH($C_1$-$C_6$ alkyl), —CON($C_1$-$C_6$ alkyl)$_2$, —CONH—OH, —CONH—OCO($C_1$-$C_6$ alkyl), —CONH—$NH_2$, —N($R_9$)$SO_2R_9$, —$SO_2N(R_9)_2$, —N(CO)NHSO$_2$CH$_3$, tetrazole, isoxazole, hydroxyisoxazole, and oxazolidinedione;
each $R_9$ is independently selected from the group consisting of hydrogen, $C_1$-$C_6$ alkyl, aryl, and heteroaryl;
$R_2$ is halogen, $C_1$-$C_6$ alkyl, $C_1$-$C_6$ haloalkyl, hydroxy ($C_1$-$C_6$ alkyl), alkoxy ($C_1$-$C_6$ alkyl), amino ($C_1$-$C_6$ alkyl), or —CN;
$R_3$ is hydrogen, halogen, $C_1$-$C_6$ alkyl, or $C_1$-$C_6$ haloalkyl;
$R_4$ and $R_5$ are independently $C_1$-$C_6$ alkyl or $C_1$-$C_6$ haloalkyl, or $R_4$ and $R_5$ are together with the carbon atoms to which they are attached form $C_3$-$C_6$ cycloalkyl optionally substituted with one or more $R_8$;
$R_6$ and $R_7$ are independently $C_1$-$C_6$ alkyl or $C_1$-$C_6$ haloalkyl, or $R_6$ and $R_7$ are together with the carbon atoms to which they are attached form $C_3$-$C_6$ cycloalkyl optionally substituted with one or more $R_8$;
wherein each $R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;
provided that when each of $R_2$, $R_4$, $R_5$, $R_6$, and $R_7$ are independently methyl, then $R_3$ is not hydrogen.

In certain embodiments, the compounds of formula (I) exclude a compound wherein: $R_1$ is —$CO_2H$, $R_2$ and $R_3$ are independently H, and $R_4$, $R_5$, $R_6$, and $R_7$ are independently methyl.

In some embodiments, the compounds of formula (I) as otherwise described herein are those wherein two R groups and the carbon atom to which they are attached form =$CH_2$. Such compounds are of formula (I-1):

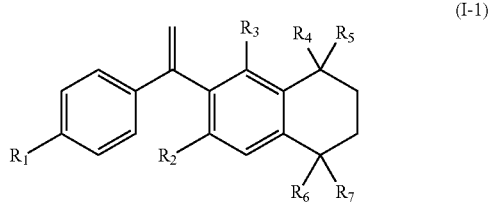

(I-1)

In some embodiments, the compounds of formula (I) as otherwise described herein are those wherein two R groups and the carbon atom to which they are attached form cyclopropyl ring. Such compounds are of formula (I-2):

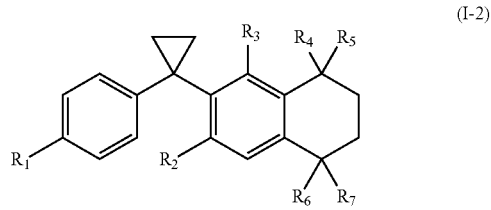

(I-2)

In some embodiments, the compounds of formula (I), (I-1), or (I-2) as otherwise described herein are those wherein $R_1$ is $CO_2H$, —$CO_2(C_1$-$C_6$ alkyl), —$CONH_2$, —CONH($C_1$-$C_6$ alkyl), or —CON($C_1$-$C_6$ alkyl)$_2$. In one embodiment, the disclosure provides compounds of formula (I), (I-1), or (I-2) as otherwise described herein where $R_1$ is $CO_2H$ or —$CO_2(C_1$-$C_6$ alkyl). In one embodiment, the disclosure provides compounds of formula (I), (I-1), or (I-2) as otherwise described herein where $R_1$ is —$CO_2H$.

In some embodiments, the compounds of formula (I), (I-1), or (I-2) as otherwise described herein are those wherein $R_2$ is halogen, $C_1$-$C_6$ alkyl, or $C_1$-$C_6$ haloalkyl. In one embodiment, the disclosure provides compounds of formula (I), (I-1), or (I-2) as otherwise described herein where $R_2$ is halogen. In one embodiment, the disclosure provides compounds of formula (I), (I-1), or (I-2) as otherwise described herein where $R_2$ is $C_1$-$C_6$ alkyl or $C_1$-$C_6$ haloalkyl. In one embodiment, the disclosure provides compounds of formula (I), (I-1), or (I-2) as otherwise described herein where $R_2$ is $C_1$-$C_6$ alkyl. In one embodiment, the disclosure provides compounds of formula (I), (I-1), or (I-2) as otherwise described herein where $R_2$ is methyl. In one embodiment, the disclosure provides compounds of formula (I), (I-1), or (I-2) as otherwise described herein where $R_2$ is $C_1$-$C_6$ haloalkyl. In one embodiment, the disclosure provides compounds of formula (I), (I-1), or (I-2) as otherwise described herein where $R_2$ is $C_1$-$C_2$ haloalkyl. In one embodiment, the disclosure provides compounds of formula (I), (I-1), or (I-2) as otherwise described herein where $R_2$ is $C_1$ haloalkyl. In one embodiment, the disclosure provides compounds of formula (I), (I-1), or (I-2) as otherwise described herein where $R_2$ is difluoromethyl.

Another embodiment of the disclosure provides compounds of formula (I)-(I-2) as otherwise described herein where $R_3$ is hydrogen or halogen. In certain embodiments of the disclosure, $R_3$ is hydrogen. In certain embodiments of the disclosure, $R_3$ is halogen. For example, in certain embodiments of the disclosure, $R_3$ is fluoro.

Another embodiment of the disclosure provides compounds of formula (I)-(I-2) as otherwise described herein where $R_4$ and $R_5$ are together with the carbon atoms to which they are attached form $C_3$-$C_6$ cycloalkyl optionally substituted with one or more $R_8$. In certain embodiments of the disclosure, $R_4$ and $R_5$ are together with the carbon atoms to which they are attached form cyclopropyl optionally substituted with one or more $R_8$. In certain embodiments of the disclosure, $R_4$ and $R_5$ are together with the carbon atoms to which they are attached form unsubstituted cyclopropyl.

In some embodiments, the compounds of formula (I), (I-1), or (I-2) as otherwise described herein are those wherein $R_4$ and $R_5$ are independently $C_1$-$C_6$ alkyl.

In some embodiments, the compounds of formula (I), (I-1), or (I-2) as otherwise described herein are those wherein $R_4$ and $R_5$ are independently methyl.

Another embodiment of the disclosure provides compounds of formula (I)-(I-2) as otherwise described herein where $R_6$ and $R_7$ together with the carbon atoms to which they are attached form $C_3$-$C_6$ cycloalkyl optionally substituted with one or more $R_8$. In certain embodiments of the disclosure, $R_6$ and $R_7$ are together with the carbon atoms to which they are attached form cyclopropyl optionally substituted with one or more $R_8$. In certain embodiments of the disclosure, $R_6$ and $R_7$ are together with the carbon atoms to which they are attached form unsubstituted cyclopropyl.

In some embodiments, the compounds of formula (I), (I-1), or (I-2) as otherwise described herein are those where $R_6$ and $R_7$ are independently $C_1$-$C_6$ alkyl. In certain embodiments, $R_6$ and $R_7$ are independently methyl.

In one embodiment of the disclosure, the compounds of formula (I)-(I-2) as otherwise described herein are those where $R_4$ and $R_5$ together with the carbon atoms to which they are attached form $C_3$-$C_6$ cycloalkyl optionally substituted with one or more $R_8$; and $R_6$ and $R_7$ are independently $C_1$-$C_6$ alkyl or $C_1$-$C_6$ haloalkyl.

In certain non-limiting example embodiments, the compounds of formula (I)-(I-2) as otherwise described herein are selected from the following group:

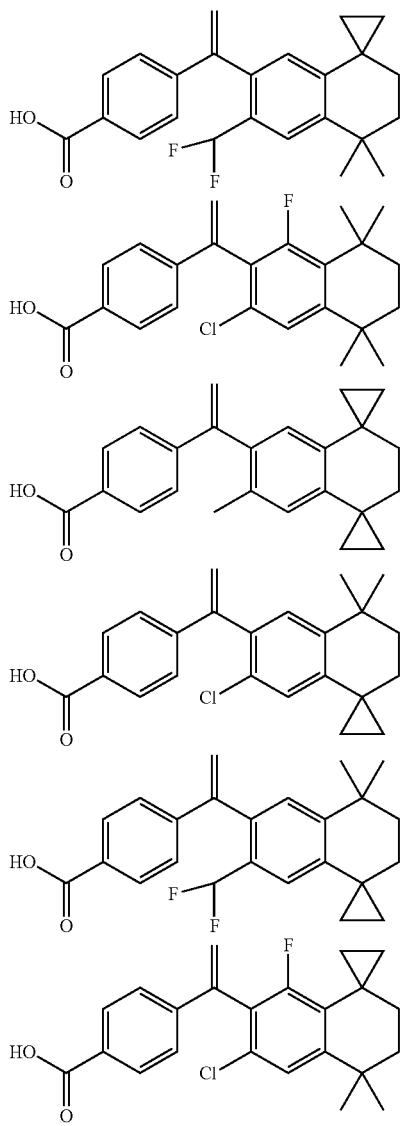

-continued

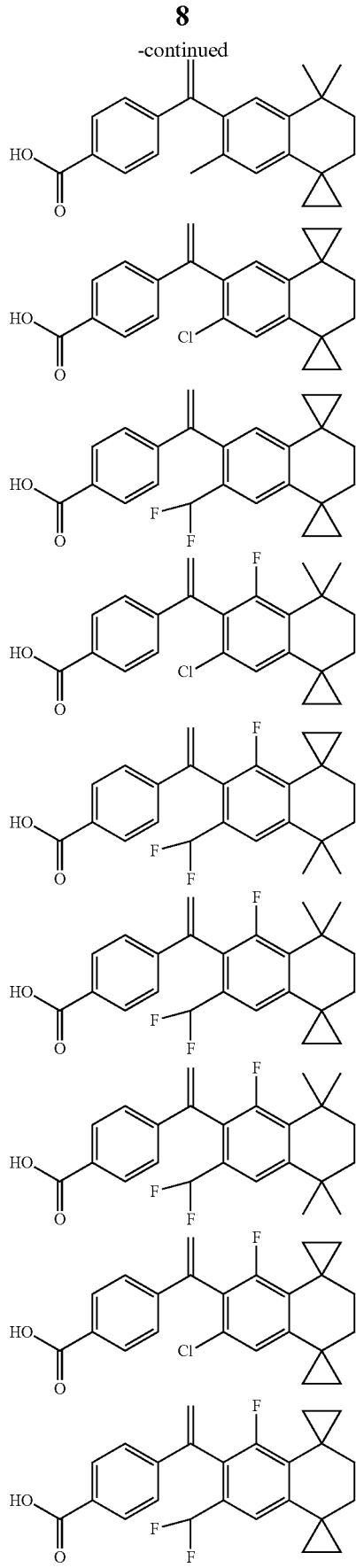

and pharmaceutically acceptable salts, esters, amides, and prodrugs thereof.

In certain non-limiting example embodiments, the compounds of formula (I), (I-1), or (I-2) as otherwise described herein are selected from the following group:

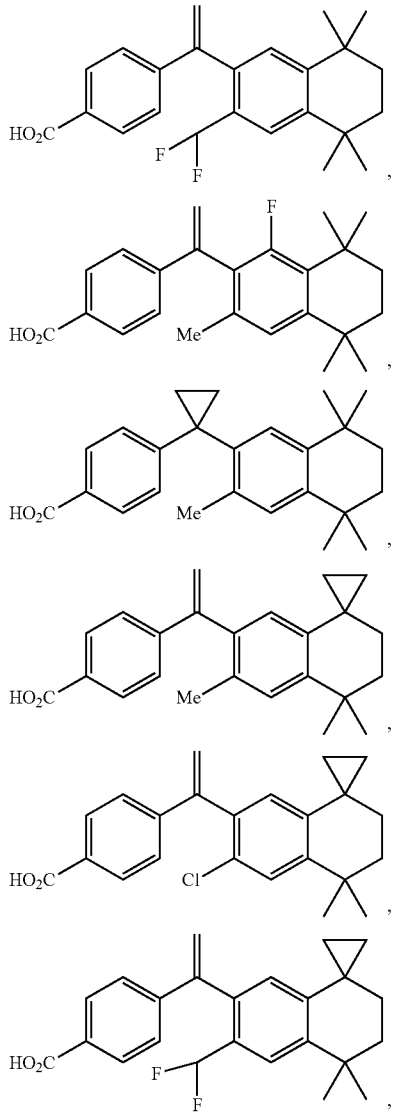

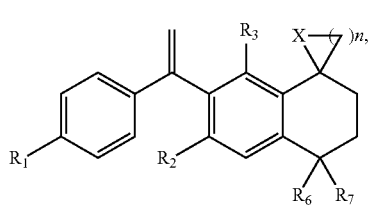

and pharmaceutically acceptable salts, esters, amides, and prodrugs thereof.

As provided above, another aspect of the disclosure provides a compound of formulae (II-1) to (II-6):

(II-1)

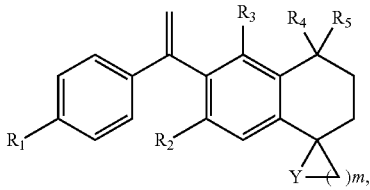

(II-2)

(II-3)

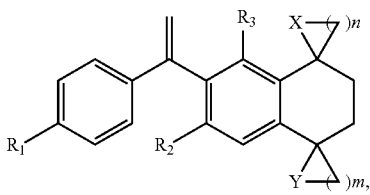

(II-4)

(II-5)

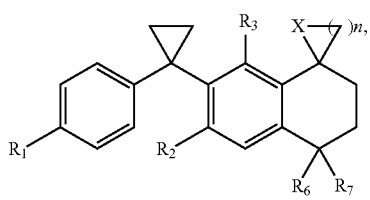

or, (II-6)

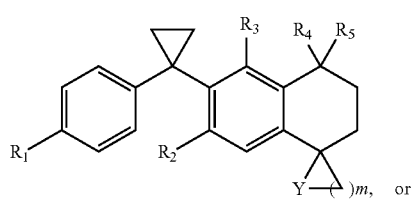

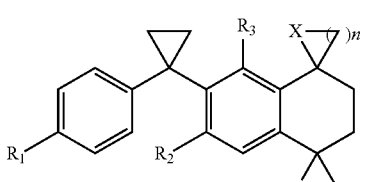

or pharmaceutically acceptable salts, esters, amides, and prodrugs thereof, wherein X is $CH_2$, O, or NH;

y is $CH_2$, O, or NH;

m is an integer 1 to 4;

n is an integer 1 to 4;

$R_1$ is selected from the group consisting of —$CO_2H$, —$CO_2(C_1$-$C_6$ alkyl), —$CO_2(arylC_1$-$C_6$ alkyl), —$CO_2$(aryl), —CHO, —$CONH_2$, —$CONH(C_1$-$C_6$ alkyl), —$CON(C_1$-$C_6$ alkyl)$_2$, —CONH—OH, —CONH—OCO($C_1$-$C_6$ alkyl), —CONH—$NH_2$, —$N(R_9)SO_2R_9$, —$SO_2N(R_9)_2$, —N(CO)$NHSO_2CH_3$, tetrazole, isoxazole, hydroxyisoxazole, and oxazolidinedione;

each $R_9$ is independently selected from the group consisting of hydrogen, $C_1$-$C_6$ alkyl, aryl, and heteroaryl;

$R_2$ is halogen, $C_1$-$C_6$ alkyl, $C_1$-$C_6$ haloalkyl, hydroxy ($C_1$-$C_6$ alkyl), alkoxy ($C_1$-$C_6$ alkyl), amino ($C_1$-$C_6$ alkyl), or —CN;

$R_3$ is hydrogen, halogen, $C_1$-$C_6$ alkyl, or $C_1$-$C_6$ haloalkyl;

$R_4$ and $R_5$ are independently $C_1$-$C_6$ alkyl or $C_1$-$C_6$ haloalkyl, or $R_4$ and $R_5$ are together with the carbon atoms to which they are attached form $C_3$-$C_6$ cycloalkyl optionally substituted with one or more $R_8$;

$R_6$ and $R_7$ are independently $C_1$-$C_6$ alkyl or $C_1$-$C_6$ haloalkyl, or $R_6$ and $R_7$ are together with the carbon atoms to which they are attached form $C_3$-$C_6$ cycloalkyl optionally substituted with one or more $R_8$;

wherein each $R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy.

In some embodiments, the compounds of formula (II-1)-(II-6) as otherwise described herein are those wherein $R_1$ is $CO_2H$, —$CO_2$($C_1$-$C_6$ alkyl), —$CONH_2$, —CONH($C_1$-$C_6$ alkyl), or —CON($C_1$-$C_6$ alkyl)$_2$. In one embodiment, the disclosure provides compounds of formula (II-1)-(II-6) as otherwise described herein where $R_1$ is $CO_2H$ or —$CO_2$($C_1$-$C_6$ alkyl). In one embodiment, the disclosure provides compounds of formula (II-1)-(II-6) as otherwise described herein where $R_1$ is $CO_2H$.

In some embodiments, the compounds of formula (II-1)-(II-6) as otherwise described herein are those wherein $R_2$ is halogen, $C_1$-$C_6$ alkyl, or $C_1$-$C_6$ haloalkyl. In one embodiment, the disclosure provides compounds of formula (II-1)-(II-6) as otherwise described herein where $R_2$ is halogen. In one embodiment, the disclosure provides compounds of formula (II-1)-(II-6) as otherwise described herein where $R_2$ is $C_1$-$C_6$ alkyl or $C_1$-$C_6$ haloalkyl. In one embodiment, the disclosure provides compounds of formula (II-1)-(II-6) as otherwise described herein where $R_2$ is $C_1$-$C_6$ alkyl. In one embodiment, the disclosure provides compounds of formula (II-1)-(II-6) as otherwise described herein where $R_2$ is methyl. In one embodiment, the disclosure provides compounds of formula (II-1)-(II-6) as otherwise described herein where $R_2$ is $C_1$-$C_6$ haloalkyl. In one embodiment, the disclosure provides compounds of formula (II-1)-(II-6) as otherwise described herein where $R_2$ is $C_1$-$C_2$ haloalkyl. In one embodiment, the disclosure provides compounds of formula (II-1)-(II-6) as otherwise described herein where $R_2$ is $C_1$ haloalkyl. In one embodiment, the disclosure provides compounds of formula (II-1)-(II-6) as otherwise described herein where $R_2$ is difluoromethyl.

Another embodiment of the disclosure provides compounds of formula (II-1)-(II-6) as otherwise described herein where $R_3$ is hydrogen or halogen. In certain embodiments of the disclosure, $R_3$ is hydrogen. In certain embodiments of the disclosure, $R_3$ is halogen. For example, in certain embodiments of the disclosure, $R_3$ is fluoro.

Another embodiment of the disclosure provides compounds of formula (II-1)-(II-6) as otherwise described herein where $R_4$ and $R_5$ are together with the carbon atoms to which they are attached form $C_3$-$C_6$ cycloalkyl optionally substituted with one or more $R_8$. In certain embodiments of the disclosure, $R_4$ and $R_5$ are together with the carbon atoms to which they are attached form cyclopropyl optionally substituted with one or more $R_8$. In certain embodiments of the disclosure, $R_4$ and $R_5$ are together with the carbon atoms to which they are attached form unsubstituted cyclopropyl.

In some embodiments, the compounds of formula (II-1)-(II-6) as otherwise described herein are those wherein $R_4$ and $R_5$ are independently $C_1$-$C_6$ alkyl. In some embodiments, the compounds of formula (II-1)-(II-6) as otherwise described herein are those wherein $R_4$ and $R_5$ are independently methyl.

Another embodiment of the disclosure provides compounds of formula (II-1)-(II-6) as otherwise described herein where $R_6$ and $R_7$ together with the carbon atoms to which they are attached form $C_3$-$C_6$ cycloalkyl optionally substituted with one or more $R_8$. In certain embodiments of the disclosure, $R_6$ and $R_7$ are together with the carbon atoms to which they are attached form cyclopropyl optionally substituted with one or more $R_8$. In certain embodiments of the disclosure, $R_6$ and $R_7$ are together with the carbon atoms to which they are attached form unsubstituted cyclopropyl.

In some embodiments, the compounds of formula (II-1)-(II-6) as otherwise described herein are those where $R_6$ and $R_7$ are independently $C_1$-$C_6$ alkyl. In certain embodiments, $R_6$ and $R_7$ are independently methyl.

In one embodiment of the disclosure, the compounds of formula (II-1)-(II-6) as otherwise described herein are those where $R_4$ and $R_5$ together with the carbon atoms to which they are attached form $C_3$-$C_6$ cycloalkyl optionally substituted with one or more $R_8$; and $R_6$ and $R_7$ are independently $C_1$-$C_6$ alkyl or $C_1$-$C_6$ haloalkyl.

The compounds of the invention include pharmaceutically acceptable salts, esters, amides, and prodrugs thereof, including but not limited to carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

Examples of pharmaceutically acceptable, non-toxic esters of the compounds of this invention include $C_1$-$C_6$ alkyl esters, wherein the alkyl group is a straight or branched, substituted or unsubstituted, $C_5$-$C_7$ cycloalkyl esters, as well as arylalkyl esters such as benzyl and triphenylmethyl. $C_1$-$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

Therapeutics Applications

The disclosure also provides methods of treating cancer. Such method includes administering to a subject in need of such treatment an effective amount of one or more compounds of the disclosure as described herein (i.e., compounds of formula (I), (I-1), (I-2), (II-1) to (II-6)) or a pharmaceutical composition of the disclosure as described herein.

Many different cancers can be treated with compounds and compositions of the disclosure. Particularly suitable cancer includes a hematological malignancy, such as leukemia or lymphoma. In certain embodiments, the cancer is acute myeloid leukemia (AML), chronic myeloid leukemia (CML), acute lymphoblastic leukemia (ALL), or chronic lymphocytic leukemia (CLL). In certain embodiments, the cancer is B cell non-Hodgkins lymphoma, T cell non-Hodgkins lymphoma, Hodgkin lymphoma, or cutaneous T cell lymphoma.

In certain embodiments, the cancer is a non-hematological solid tumor. Examples of such solid tumors include, but are not limited to, carcinomas, sarcomas, and astrocytomas. In certain embodiments, the cancer is breast cancer, prostate cancer, lung cancer (e.g., small-cell lung carcinoma (SCLC) and non-small-cell lung carcinoma (NSCLC)), gastric cancer, colorectal cancer, cervical cancer, endometrial cancer, ovarian cancer, skin cancer (e.g., basal-cell skin cancer (BCC), squamous-cell skin cancer (SCC), and melanoma), pancreatic cancer, kidney cancer, adrenal gland cancer, sarcoma, glioblastoma, or neuroblastoma, or lymphoma.

The disclosure also provides methods of treating autoimmune disorders. Such methods include administering to a subject in need thereof an effective amount of the compound of the disclosure as described herein or the pharmaceutical composition of the disclosure as described herein. In certain embodiments, the autoimmune disorder is psoriasis. In certain embodiments, the autoimmune disorder is hyperthyroidism.

Another aspect of the disclosure provides methods for treating skin dermatitis. Such methods include administering to a subject in need thereof an effective amount of the compound of the disclosure as described herein or the pharmaceutical composition of the disclosure as described herein. In certain embodiments, skin dermatitis is eczema or hand dermatitis.

Another aspect of the disclosure provides methods for increasing peripheral blood counts and/or improving immune system function. Such methods include administering to a subject in need thereof an effective amount of the compound of the disclosure as described herein or the pharmaceutical composition of the disclosure as described herein. In certain embodiments, the subject in need thereof has a disorder including but not limited to myelodysplastic syndrome, idiopathic thrombocytopenic purpura, cytopenias due to bone marrow involvement with malignancy, congenital neutropenia, and aplastic anemia.

The compounds and compositions of the disclosure as described herein may also be administered in combination with one or more secondary therapeutic agents. Thus, in certain embodiment, the method also includes administering to a subject in need of such treatment an effective amount of one or more compounds of the disclosure as described herein (i.e., compounds of formula (I), (I-1), (I-2), (II-1) to (II-6)) or a pharmaceutical composition of the disclosure as described herein and one or more secondary therapeutic agents. Examples of suitable secondary therapeutic agents include, but are not limited to, camptothecin, doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, and abt-737. In certain embodiments, the secondary therapeutic agent is an immunotherapy agent. Examples of suitable immunotherapy agents include, but are not limited to PD-1 antibodies (such as nivolumab, pembrolizumab, pidilizumab, etc.), chimeric antigen receptor (CAR) T cell therapy, Bispecific T cell Engager (BiTE®) antibodies, and other therapeutic monoclonal antibodies. When administered as a combination, the compounds and compositions of the disclosure as described herein and the secondary therapeutic agents can be formulated as separate compositions that are given simultaneously or sequentially, or the therapeutic agents can be given as a single composition. In certain embodiments, the secondary therapeutic agent may be administered in an amount below its established half maximal inhibitory concentration ($IC_{50}$). For example, the secondary therapeutic agent may be administered in an amount less than 1% of, e.g., less than 10%, or less than 25%, or less than 50%, or less than 75%, or even less than 90% of the inhibitory concentration ($IC_{50}$).

Pharmaceutical Compositions

In one embodiment, the disclosure provides pharmaceutical compositions comprising a compound as described above and at least one pharmaceutically acceptable carrier, solvent, adjuvant or diluent.

For administration, the compounds are ordinarily combined with one or more adjuvants appropriate for the indicated route of administration. The compounds may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The compounds of the invention can be administered as the sole active pharmaceutical agent, or they can be used in combination with one or more other compounds useful for carrying out the methods of the invention. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

The compounds of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and pharmaceutical compositions of the present invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds and pharmaceutical compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Dosage levels of the order of from about 0.01 mg to about 50 mg per kilogram of body weight per day, and more preferably between 0.1 mg to about 50 mg per kilogram of body weight per day, are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly, arylalkyl and alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, and —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms at any available position.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl" as used herein, mean a monocyclic heterocycle or a bicyclic heterocycle. The monocyclic heterocycle is a 3, 4, 5, 6 or 7 membered-ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5-membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, $4^{th}$ Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed.

L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I), (I-1), (I-2), or (II-1)-(II-6) can be prepared according to general procedures (below), and/or analogous synthetic procedures. One of skill in the art can adapt the reaction sequences of Examples 1-6 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

EXAMPLES

The preparation of the compounds of the disclosure is illustrated further by the following examples, which are not to be construed as limiting the disclosure in scope or spirit to the specific procedures and compounds described in them.

General Experimental

All reagents were commercially available and used "as is" without further purification or drying. $^1$H-NMR spectra were obtained on a Bruker Ultrashield 400 (400 MHz) instrument. Prep-HPLC purifications were performed on an Agela HS-1000T instrument utilizing acetonitrile/water as eluent. LC/MS analyses were performed on a SHIMADZU LCMS-2020EV using a Kinetex 2.6 um EVO C18 100 A, 50 mm×3.0 mm, 2.6 um column. The standard gradient used was 10% ACN/H$_2$O to 95% ACN/H$_2$O. The aqueous phase was buffered with 5 mM ammonium bicarbonate.

Example 1: Preparation of 4-(1-(6'-(difluoromethyl)-4',4'-dimethyl-3',4'-dihydro-2'H-spiro[cyclopropane-1,1'-naphthalen]-7'-yl)vinyl)benzoic Acid (DSP-109; or 109)

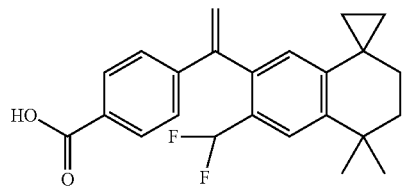

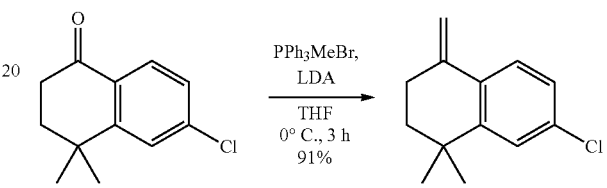

To a −10° C. solution of bromo(methyl)triphenyl-[5]-phosphane (89.3 g, 250 mmol, 2.6 eq.) in THF (1 L) under a nitrogen atmosphere was added LDA (2 M in THF, 145 mL, 3.0 eq.) over 30 minutes. To the resulting solution was added 6-chloro-4,4-dimethyl-1,2,3,4-tetrahydronaphthalen-1-one (20 g, 95.8 mmol, 1.0 eq.) over 30 minutes. The resulting solution was stirred at 0° C. for 3 h, then quenched by the addition of 1000 g of ice/H$_2$O. The resulting mixture was extracted with CH$_2$Cl$_2$ (3×500 mL). The combined organic layers were dried (Na$_2$SO$_4$) and concentrated. The residue was purified by silica gel chromatography eluting with petroleum ether to give 18 g (91%) of 7-chloro-1,1-dimethyl-4-methylidene-1,2,3,4-tetrahydronaphthalene as colorless oil.

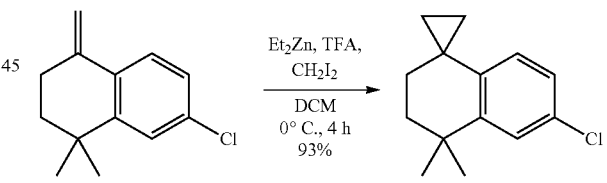

To a solution of diethylzinc (106.6 g, 863 mmol, 10 eq.) in dichloromethane (650 mL) at 0° C. was added trifluoroacetic acid (84.7 g, 864 mmol, 10 eq.) over 20 minutes. The resulting solution was stirred at 0° C. for 1 h whereupon diiodomethane (233.9 g, 873 mmol, 10 eq.) was added over 20 minutes. The resulting solution was stirred at 0° C. for 1 h whereupon 7-chloro-1,1-dimethyl-4-methylidene-1,2,3,4-tetrahydronaphthalene (18 g, 87 mmol, 1.0 eq.) was added over 30 minutes. The resulting solution was stirred at 0° C. for 4 h, then quenched by the addition of saturated aqueous sodium bicarbonate (600 mL). The mixture was extracted with CH$_2$Cl$_2$ (3×300 mL). The organic layers were combined, washed with brine, then concentrated under reduced pressure to give 17.8 g (93%) of 6-chloro-4,4-dimethyl-3,4-dihydro-2H-spiro[cyclopropane-1,1-naphthalene] as colorless oil.

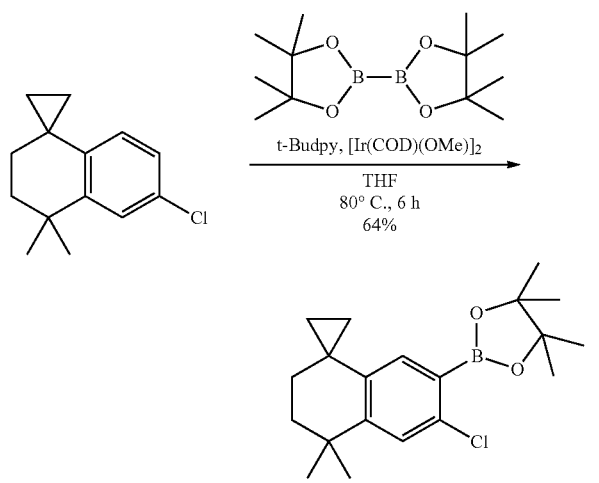

A mixture of 6-chloro-4,4-dimethyl-3,4-dihydro-2H-spiro[cyclopropane-1,1-naphthalene] (5 g, 23 mmol, 1.0 eq.), 2-methyl(2-H)propane pyridine (616 mg, 2.3 mmol, 0.1 eq.), 4,4,5,5-tetramethyl-2-(tetramethyl-1,3,2-dioxaborolan-2-yl)-1,3,2-dioxaborolane (8.66 g, 34 mmol, 1.5 eq.), [Ir(COD)(OMe)]$_2$ (760 mg, 1.15 mmol, 0.05 eq.) in THF (125 mL) was heated at 80° C. under a nitrogen atmosphere for 6 h, then cooled to rt and concentrated to a volume of ca. 30 mL. The crude mixture was purified by preparative RP-HPLC eluting with ACN/H$_2$O (60%-90% 30 min) to give 5 g (64%) of 2-(6-chloro-4,4-dimethyl-3,4-dihydro-2H-spiro[cyclopropane-1,1-naphthalen]-7-yl)-4,4,5,5-tetramethyl-1,3,2-dioxaborolane as a white solid.

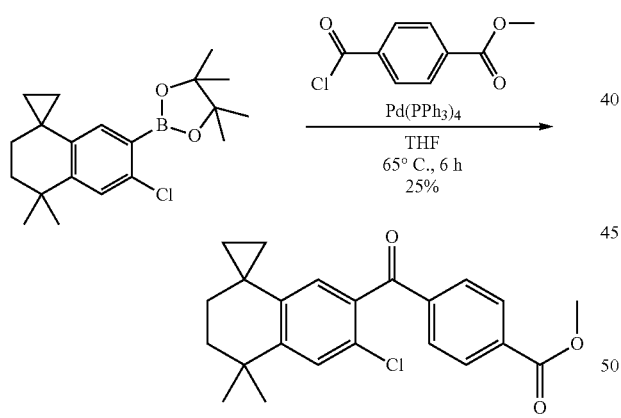

A mixture of 2-(6-chloro-4,4-dimethyl-3,4-dihydro-2H-spiro[cyclopropane-1,1-naphthalen]-7-yl)-4,4,5,5-tetramethyl-1,3,2-dioxaborolane (5 g, 14.4 mmol, 1.0 eq.), methyl 4-(carbonochloridoyl)benzoate (4.31 g, 21.7 mmol, 1.5 equiv), K$_3$PO$_4$ (4.03 g, 29.0 mmol, 2.0 eq.), and tetrakis(triphenylphosphane) palladium (1.74 g, 1.5 mmol, 0.1 equiv) in THF (100 mL) and H$_2$O (50 mL) was heated at 65° C. for 6 h then cooled to room temperature and concentrated to a volume of ca. 20 mL. The crude mixture was purified by preparative RP-HPLC eluting with ACN/H$_2$O (60%-90% 30 min) to give 1.3 g (25%) of methyl 4-(6-chloro-4,4-dimethyl-3,4-dihydro-2H-spiro[cyclopropane-1,1-naphthalene]-7-carbonyl)benzoate as a yellow solid.

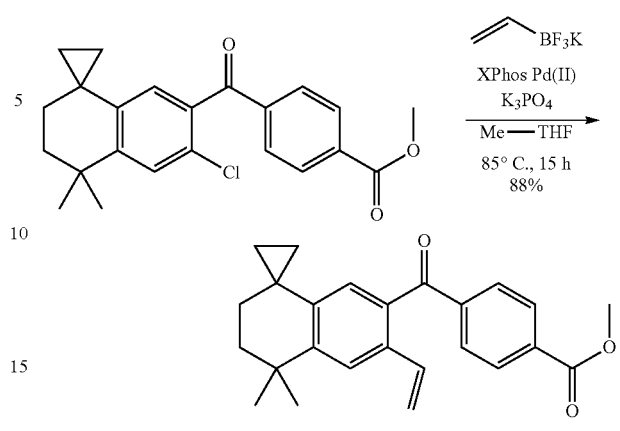

A mixture of K$_3$PO$_4$ (1.27 g, 6.0 mmol, 3.0 eq.), potassium trifluoro(vinyl)borate (0.332 g, 2.4 mmol, 1.2 eq.), methyl 4-([6-chloro-4,4-dimethyl-3,4-dihydro-2H-spiro[cyclopropane-1,1-naphthalene]-7-yl]carbonyl)benzoate (0.7 g, 1.8 mmol, 1.0 eq.), XPhosPd(II) (158 mg, 0.2 mmol, 0.1 eq.) in 2-methyl THF (20 mL) was heated at 85° C. for 15 h then cooled to room temperature. The crude mixture was purified by preparative RP-HPLC eluting with ACN/H$_2$O (60%-90% 30 min) to give 0.6 g (88%) of methyl 4-([6-ethenyl-4,4-dimethyl-3,4-dihydro-2H-spiro[cyclopropane-1,1-naphthalene]-7-yl]carbonyl)benzoate as a white solid.

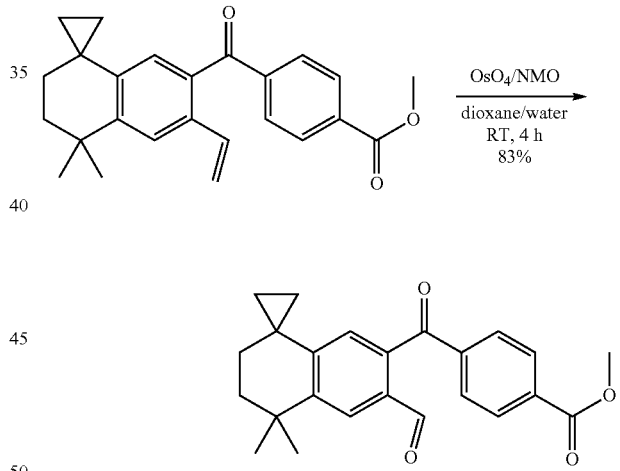

To a solution of methyl 4-([6-ethenyl-4,4-dimethyl-3,4-dihydro-2H-spiro[cyclopropane-1,1-naphthalene]-7-yl]carbonyl)benzoate (0.6 g, 1.6 mmol, 1.0 eq.) in dioxane (5 mL) was added water (2.4 mL), 2,6-dimethylpyridine (0.34 g, 3.7 mmol, 2.0 eq.), sodium periodate (1.72 g, 8.0 mmol, 5.0 eq.), and osmium tetroxide (102 mg, 0.4 mmol, 0.2 eq.). The resulting solution was stirred at room temperature for 4 h, then quenched by the addition of 10% aq Na$_2$SO$_3$ (50 mL). The mixture was extracted with EtOAc (3×50 mL) and the combined extracts were washed with brine, dried (Na$_2$SO$_4$) and concentrated. The residue was purified by silica gel chromatography eluting with EtOAc/petroleum ether (1:20) to give 0.5 g (83%) of methyl 4-([6-formyl-4,4-dimethyl-3,4-dihydro-2H-spiro[cyclopropane-1,1-naphthalene]-7-yl]carbonyl)benzoate as a white solid.

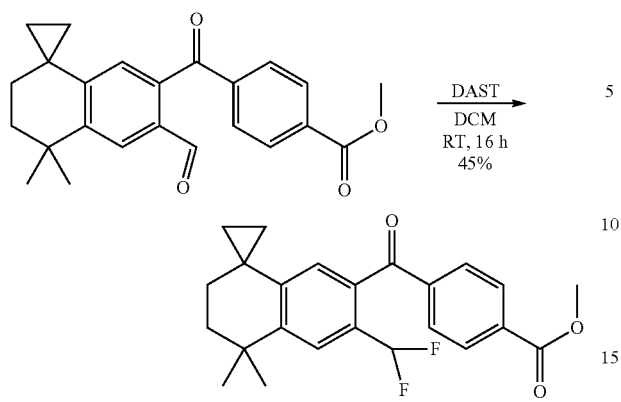

To a solution of methyl 4-(6-formyl-4,4-dimethyl-3,4-dihydro-2H-spiro[cyclopropane-1,1-naphthalene]-7-carbonyl)benzoate (0.5 g, 1.3 mmol, 1.0 eq.) in CH$_2$Cl$_2$ (5 mL) at −10° C. was added DAST (3.22 g, 20.0 mmol, 15.0 eq.) over 5 minutes. The resulting solution was stirred at room temperature for 16 h, then quenched by the addition of saturated aqueous NaHCO$_3$ (50 mL). The mixture was extracted with CH$_2$Cl$_2$ (3×100 mL) then the organic layers were combined, dried (Na$_2$SO$_4$) and concentrated to give 0.24 g (45%) of methyl 4-(6-(difluoromethyl)-4,4-dimethyl-3,4-dihydro-2H-spiro[cyclopropane-1,1-naphthalene]-7-carbonyl)benzoate as a white solid.

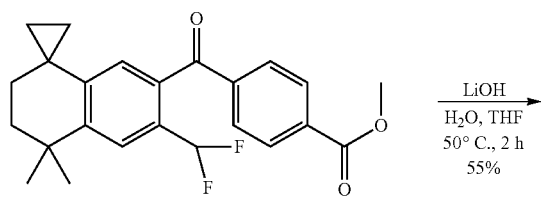

To a solution of methyl 4-(6-(difluoromethyl)-4,4-dimethyl-3,4-dihydro-2H-spiro[cyclopropane-1,1-naphthalene]-7-carbonyl)benzoate (150 mg, 0.38 mmol, 1.0 eq.) in THF (2 mL) was added LiOH (18 mg, 0.75 mmol, 2.0 eq.) in water (2 mL). The resulting mixture was heated at 50° C. for 2 h, then cooled to room temperature and the THF was removed under reduced pressure. The aqueous mixture was adjusted to pH 2 with 1M HCl, then extracted with CH$_2$Cl$_2$ (3×10 mL). The organic layers were combined, dried (Na$_2$SO$_4$), and concentrated to give 80 mg (55%) of 4-(6-(difluoromethyl)-4,4-dimethyl-3,4-dihydro-2H-spiro[cyclopropane-1,1-naphthalene]-7-carbonyl)benzoic acid as a white solid.

To a solution of magnesium methyltriphenylphosphonium bromide (1.3 g, 3.6 mmol, 17.5 eq.) in THF (1 mL) at −30° C. was added LDA (2M in THF, 1.65 mL, 15.0 eq.) over 5 minutes. To the resulting solution was added 4-(6-(difluoromethyl)-4,4-dimethyl-3,4-dihydro-2H-spiro[cyclopropane-1,1-naphthalene]-7-carbonyl)benzoic acid (80 mg, 0.21 mmol, 1.0 eq.) as a solution in THF (5 mL) over 5 minutes. The resulting solution was stirred at 0° C. for 4 h then quenched by the addition of 10 g ice/H2O. The resulting mixture was extracted with EtOAc (3×10 mL). The combined extracts were concentrated and purified by RP-HPLC eluting with ACN/H$_2$O (60%-90% 30 min) to give 35 mg (44%) of 4-(1-(6-(difluoromethyl)-4,4-dimethyl-3,4-dihydro-2H-spiro[cyclopropane-1,1-naphthalen]-7-yl)vinyl)benzoic acid as a white solid: $^1$H-NMR: (400 MHz, CDCl$_3$, ppm): δ 8.02 (d, J=8.8 Hz, 2H), 7.65 (s, 1H), 7.35 (d, J=8.4 Hz, 2H), 6.46 (t, J=55.4 Hz, 1H), 6.44 (s, 1H), 5.95 (s, 1H), 5.35 (s, 1H), 1.83-1.80 (m, 2H), 1.72-1.69 (m, 2H), 1.39 (s, 6H), 0.93-0.88 (m, 2H), 0.87-0.82 (m, 2H); $^{19}$F-NMR: (376 MHz, CDCl$_3$, ppm): δ 108.4 (s). LCMS: (ES, m/z): 381 [M−H]$^-$.

Example 2: Preparation of 4-(1-(4',4',6'-trimethyl-3',4'-dihydro-2'H-spiro[cyclopropane-1,1'-naphthalen]-7'-yl)vinyl)benzoic Acid (DPS-107; 107)

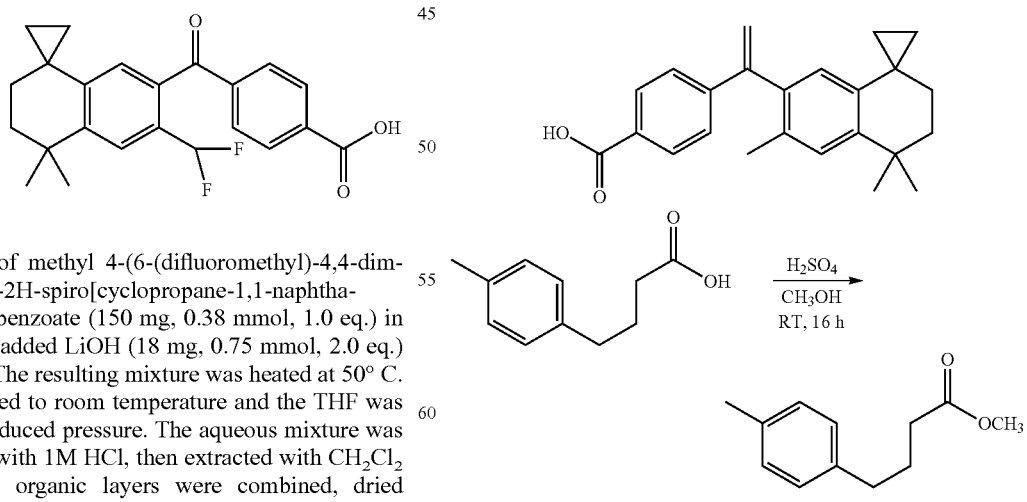

A mixture of 4-(4-methylphenyl)butanoic acid (50 g, 260 mmol, 1.0 eq.), MeOH (300 mL), and sulfuric acid (5 mL) was stirred at room temperature for 16 h, then concentrated under reduced pressure. The residue was quenched by the addition of sat. NaHCO$_3$ (200 mL) and the aqueous mixture was extracted with EtOAc (2×200 mL). The combined organic layers were washed with brine, dried (Na$_2$SO$_4$), and concentrated to give 59.1 g of methyl 4-(4-methylphenyl) butanoate as yellow oil.

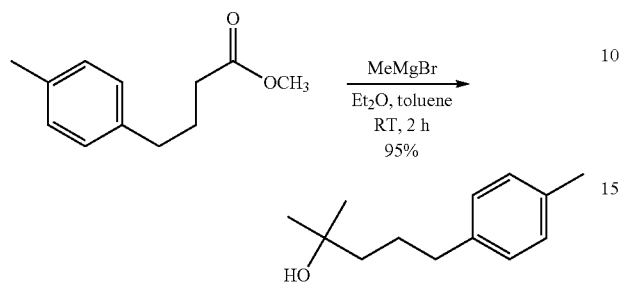

To a solution of methyl 4-(4-methylphenyl)butanoate (59.1 g, 307 mmol, 1.0 eq.) in ether (500 mL) and toluene (1 L) was added a solution of methylmagnesium bromide in ether (3 m, 246 mL, 738 mmol, 2.4 eq.). The resulting solution was stirred at room temperature for 2 h then quenched by the addition of saturated aqueous NH$_4$Cl (100 mL). The pH of the solution was adjusted to 7 with concentrated HCl and this was extracted with EtOAc (2×500 mL). The organic layers were combined, washed with brine, dried (Na$_2$SO$_4$), and concentrated to give 56.4 g (95%) of 2-methyl-5-(4-methylphenyl)pentan-2-ol as yellow oil.

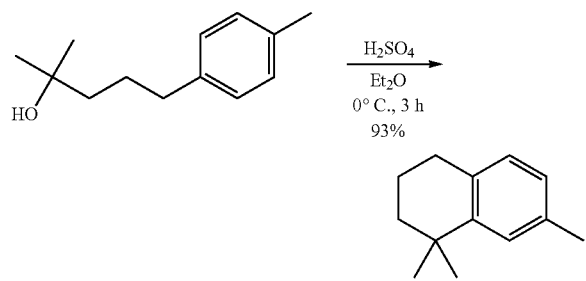

To a solution of 2-methyl-5-(4-methylphenyl)pentan-2-ol (56.4 g, 293 mmol, 1.0 eq.) in Et$_2$O at 0° C. was added concentrated H$_2$SO$_4$ (350 mL) in a dropwise fashion. The reaction mixture was stirred at 0° C. for 3 h, then quenched by the addition of saturated aqueous NaHCO$_3$ (500 mL). The organic layer was removed, and the aqueous layer was further neutralized by the addition of saturated aqueous Na$_2$CO$_3$ (500 mL). The aqueous layer was then extracted with EtOAc (2×500 mL), all organic layers were combined, washed with brine, dried (Na$_2$SO$_4$), and concentrated to give 47.3 g (93%) of 1,1,7-trimethyl-1,2,3,4-tetrahydronaphthalene as yellow oil.

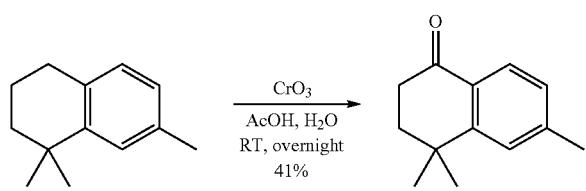

To a solution of 1,1,7-trimethyl-1,2,3,4-tetrahydronaphthalene (47.3 g, 271 mmol, 1.0 eq.) in acetic acid (200 mL) was added a solution of chromium trioxide (136 g, 1.4 mmol, 5.0 eq.) in acetic acid (542 mL) and H$_2$O (63 mL) in a dropwise fashion. The resulting solution was stirred at room temperature overnight, then quenched by the addition of i-PrOH (300 mL). The resulting mixture was concentrated under reduced pressure and the residue was treated with EtOAc (300 mL). The mixture was filtered through a pad of Celite® and the filtrate was washed with H$_2$O (3×100 mL), brine, dried (MgSO$_4$), and concentrated to give 21 g (41%) of 4,4,6-trimethyl-1,2,3,4-tetrahydronaphthalen-1-one as yellow oil.

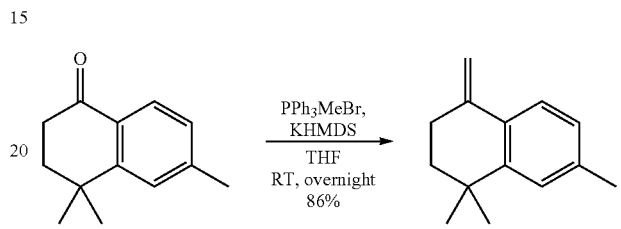

To a solution of PPh$_3$MeBr (9.7 g, 27.1 mmol, 2.6 eq.) in THF (60 mL) at −10° C. was added a solution of potassium hexamethyldisilazide in THF (1 M, 27 mL, 27 mmol, 2.6 eq.) and the resulting solution was stirred at 0° C. for 20 minutes. A solution of 4,4,6-trimethyl-1,2,3,4-tetrahydronaphthalen-1-one (2 g, 10.6 mmol, 1.0 eq.) in THF (40 mL) was then added to the ylide solution at −10° C. The reaction mixture was stirred at 0° C. for 3 h then at room temperature overnight. The reaction mixture was quenched by the addition of ice/H$_2$O (30 mL) and the resulting mixture was extracted with petroleum ether (3×60 mL). The combined organic layers were concentrated under reduced pressure and the residue was purified by silica gel chromatography eluting with petroleum ether to give 1.7 g (86%) of 1,1,7-trimethyl-4-methylidene-1,2,3,4-tetrahydronaphthalene as colorless oil.

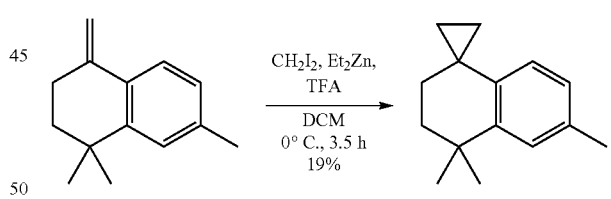

To a solution of diethylzinc in hexane (1 M, 269 mL, 269 mmol, 10 eq.) in CH$_2$Cl$_2$ (130 mL) at 0° C. was added trifluoroacetic acid (30.7 g, 269 mmol, 10 eq.) in a dropwise fashion. The solution was stirred at 0° C. for 1 h, then a solution of 1,1,7-trimethyl-4-methylidene-1,2,3,4-tetrahydronaphthalene (5 g, 26.8 mmol, 1.0 eq.) in CH$_2$Cl$_2$ (50 mL) was added. The resulting solution was stirred at 0° C. for 3.5 h, then quenched by the addition of saturated aqueous NaHCO$_3$ (200 mL). The solids were removed by filtration and the filtrate was extracted with CH$_2$Cl$_2$ (2×300 mL). The organic layers were combined and concentrated under reduced pressure. The residue was purified by reverse phase MPLC (C18 column) eluting with ACN/H$_2$O (70-90% gradient). Removal of the solvents gave 1 g (19%) of the desired spirocyclopropane as a yellow oil.

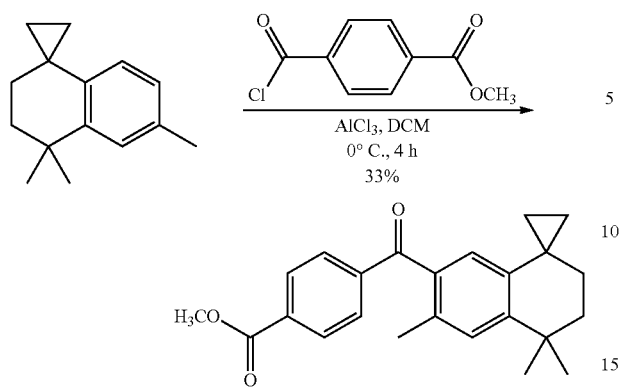

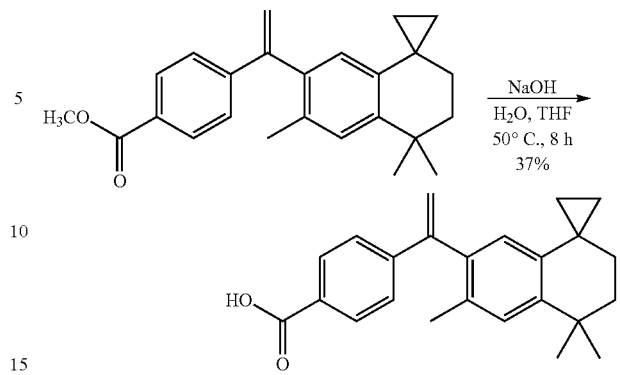

To a suspension of methyl 4-(carbonochloridoyl)benzoate (546 mg, 2.8 mmol, 1.1 eq.) and aluminum trichloride (1.2 g, 7.5 mmol, 3.0 eq.) in CH$_2$Cl$_2$ (25 mL) at 0° C. was added the spirocyclopropane from the previous step as a solution in CH$_2$Cl$_2$ (5 mL). The resulting solution was stirred at 0° C. for 4 h, then quenched by the addition of ice/H$_2$O (30 mL). The resulting mixture was extracted with EtOAc (2×20 mL) and the combined extracts were concentrated under reduced pressure. The residue was purified by reverse phase MPLC (C18 column) eluting with ACN/H$_2$O (70-100% gradient). Removal of the solvents gave 300 mg (33%) of the desired diarylketone as a light-yellow solid.

A mixture of the ester from the previous step (100 mg, 0.28 mmol, 1.0 eq.), concentrated aqueous sodium hydroxide (10 mL) and THF (10 mL) was heated at 50° C. for 8 h. The mixture was cooled to room temperature and the pH of the solution was adjusted to 5 with 1N HCl. The resulting solution was extracted with EtOAc (3×50 mL). The combined organic layers were concentrated under reduced pressure and the residue was purified by reverse phase MPLC (C18 column) eluting with ACN/H$_2$O containing 0.05% formic acid (70-85% gradient). Removal of the solvents gave 36 mg (37%) of the desired carboxylic acid as a white solid. $^1$H-NMR: (300 MHz, DMSO-d$_6$, ppm): δ 7.89-7.87 (d, J=14 Hz, 2H), 7.31-7.29 (d, J=14 Hz, 2H), 7.17 (s, 1H), 6.41 (s, 1H), 5.88 (s, 1H), 5.24 (s, 1H), 1.88 (s, 3H), 1.74-1.64 (m, 4H), 1.30 (s, 6H), 0.87 (s, 2H), 0.77 (s, 2H). LC-MS: (ES, m/z): 345.10 [M−H]$^+$.

Example 3: Preparation of 4-(1-(1-fluoro-3,5,5,8,8-pentamethyl-5,6,7,8-tetrahydronaphthalen-2-yl)vinyl)benzoic Acid (DSP-106; 106)

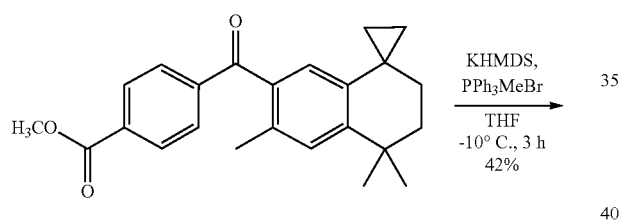

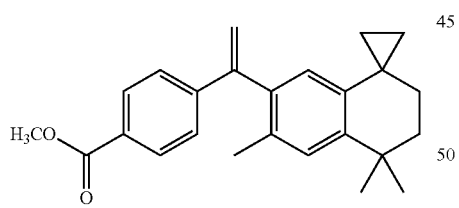

To a solution of PPh$_3$MeBr (759 mg, 2.15 mmol, 2.50 equiv.) in THF (6 mL) at −30° C. was added a solution of potassium hexamethyldisilazide in THF (1 M, 2.2 mL, 2.2 mmol, 2.5 eq.). After 30 minutes, a solution of the ketone from the previous step (300 mg, 0.86 mmol, 1.0 eq.) in THF (1 mL) was added and the resulting solution was stirred at −10° C. for 1 h. The reaction was quenched by the addition of H$_2$O (8 mL). The resulting mixture was extracted with EtOAc (2×30 mL), then the combined organic layers were washed with brine, dried (Na$_2$SO$_4$) and concentrated. The residue was purified by preparative TLC eluting with EtOAc/petroleum ether (1:50) to give 125 mg (42%) of desired alkene.

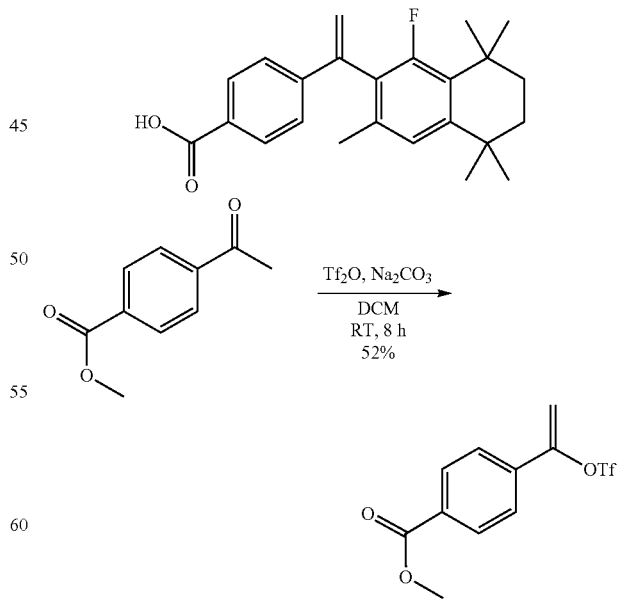

A solution of methyl 4-acetylbenzoate (17.8 g, 100 mmol, 1.0 eq.), Na$_2$CO$_3$ (17.0 g, 160 mmol, 1.6 eq.), Tf$_2$O (56.4 g, 200 mmol, 2.0 equiv.) in CH$_2$Cl$_2$ (150 mL) was stirred at room temperature for 8 h, then the solids were removed by filtration. The filtrate was treated with saturated aqueous NaHCO₃ (150 mL), then the layers were separated, and the organic was washed with brine, dried (Na₂SO₄), and concentrated to give 16 g (52%) of methyl 4-[1-[(trifluoromethane)sulfonyloxy]ethenyl]benzoate as a white solid.

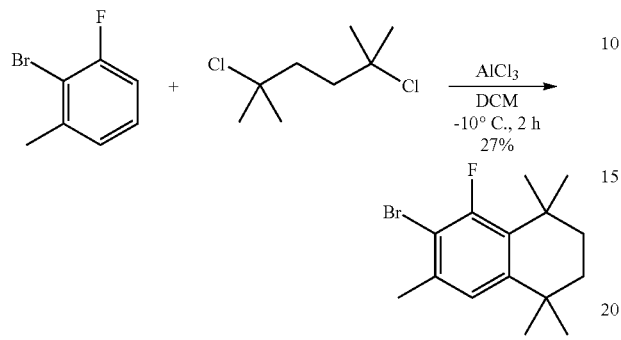

To a mixture of 2,5-dichloro-2,5-dimethylhexane (16.0 g, 87.4 mmol, 1.2 eq.), AlCl₃ (1.98 g, 17.5 mmol, 0.20 eq.) in CH₂Cl₂ (90 mL) at −10° C. was added a solution of 2-bromo-1-fluoro-3-methylbenzene (14.0 g, 74.1 mmol, 1.0 eq.) in CH₂Cl₂ (10 mL). Stirred the reaction mixture at −10° C. for 2 h then quenched by the addition of H₂O (20 mL) and saturated aqueous NaHCO₃ (50 mL). The resulting mixture was extracted with CH₂Cl₂ (100 mL), then the combined organics were dried (Na₂SO₄) and concentrated under reduced pressure to give 6 g (27%) of 6-bromo-5-fluoro-1,1,4,4,7-pentamethyl-1,2,3,4-tetrahydronaphthalene as a yellow solid.

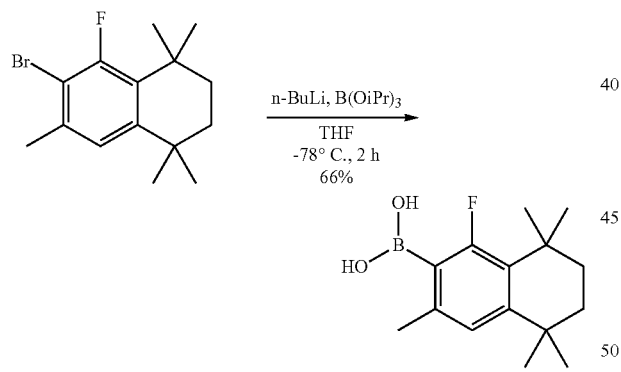

To a solution of 6-bromo-5-fluoro-1,1,4,4,7-pentamethyl-1,2,3,4-tetrahydronaphthalene (1 g, 3.3 mmol, 1.0 eq.) in THF (30 mL) at −78° C. was added n-BuLi in hexane (2.5 M, 2 mL, 5.0 mmol, 1.5 eq.) and the mixture was stirred for 1 h. To the resulting solution was added triisopropylborate (2.4 mL, 10.0 mmol, 3.0 eq.) at −78° C. The solution was then stirred an additional 2 h at −78° C., then quenched by the addition of ice/H₂O (20 mL). The mixture was extracted with EtOAc (2×50 mL), then the combined organic layers were washed with brine, dried (Na₂SO₄), and concentrated under reduced pressure. The residue was purified by silica gel chromatography eluting with EtOAc/petroleum ether (4:1) to give 0.58 g (66%) of (1-fluoro-3,5,5,8,8-pentamethyl-5,6,7,8-tetrahydronaphthalen-2-yl)boronic acid as yellow oil.

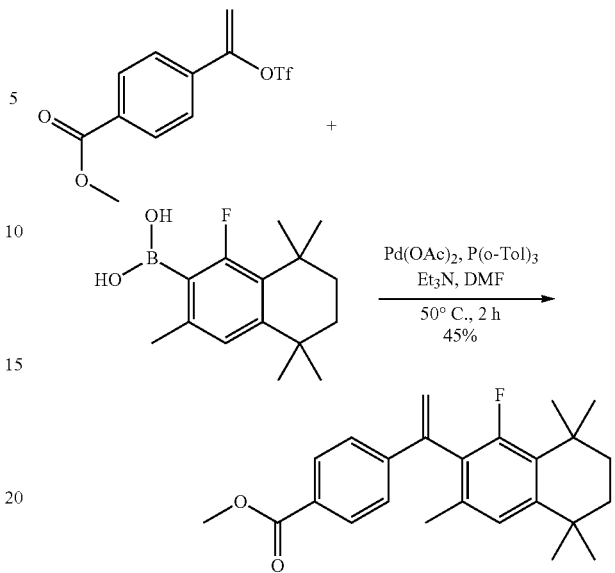

A mixture of (1-fluoro-3,5,5,8,8-pentamethyl-5,6,7,8-tetrahydronaphthalen-2-yl) boronic acid (460 mg, 1.7 mmol, 1.0 equiv.), methyl 4-[1-[(trifluoromethane)sulfonyloxy]ethenyl]benzoate (595 mg, 1.9 mmol, 1.1 equiv.), Pd(OAc)₂ (20 mg, 0.09 mmol, 0.05 equiv.), p(o-Tol)₃ (42 mg, 0.14 mmol, 0.08 equiv.), and TEA (0.5 mL) in DMF (7 mL) was stirred at 50° C. for 2 h, then cooled to room temperature and quenched by the addition of H₂O (50 mL). The mixture was extracted with EtOAc (2×50 mL), and the organic layers were washed with brine, dried (Na₂SO₄), and concentrated. The residue was purified by silica gel chromatography eluting with EtOAc/petroleum ether (10:1) to give 300 mg (45%) of methyl 4-[1-(1-fluoro-3,5,5,8,8-pentamethyl-5,6,7,8-tetrahydronaphthalen-2-yl)ethenyl]benzoate as a light-yellow solid.

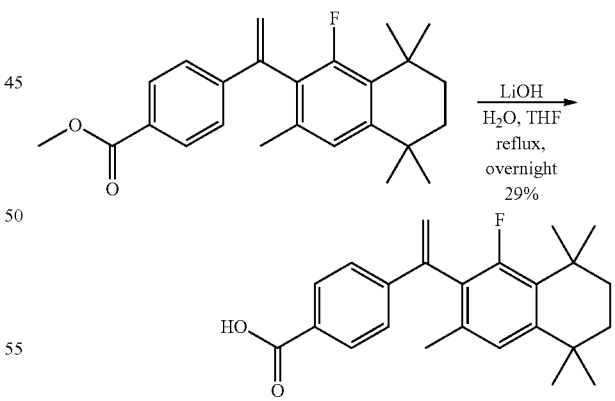

To a solution of methyl 4-[1-(1-fluoro-3,5,5,8,8-pentamethyl-5,6,7,8-tetrahydronaphthalen-2-yl)ethenyl]benzoate (215 mg, 0.57 mmol, 1.0 eq.) in THF (7 mL) as added a solution of concentrated aqueous LiOH (7 mL). The resulting mixture was heated at reflux overnight, then cooled to room temperature and the pH of the solution was adjust to 5 by the action of 1 N HCl. The aqueous mixture was extracted with EtOAc (2×20 mL), then the combined layers were concentrated under reduced pressure and the reside was purified by reverse phase chromatography (XSelect CSK C18 OBD column, 19×250 nm, 5 μm; mobile phase A: H2O (0.05% TFA), mobile phase B: ACN; flow rate: 25 mL/min, Gradient: 32% ACN to 68% ACN over 12 min, Detector: UV 254, 220 nm). Removal of the solvents gave 60 mg (29%) of 4-[1-(1-fluoro-3,5,5,8,8-pentamethyl-5,6,7,8-tetrahydronaphthalen-2-yl)ethenyl]benzoic acid as a white solid: $^1$H-NMR: (300 MHz, CDCl$_3$, ppm): δ 7.95 (d, J=14 Hz, 2H), 7.36 (d, J=14 Hz, 2H), 7.07 (s, 1H), 6.12 (s, 1H), 5.27 (s, 1H), 2.05 (s, 3H), 1.73-1.67 (m, 4H), 1.33-1.31 (m, 12H). LC-MS: (ES, m/z): 367.30 [M+H]$^+$.

Example 4: Preparation of 4-(1-(3-(difluoromethyl)-5,5,8,8-tetramethyl-5,6,7,8-tetrahydronaphthalen-2-yl)vinyl)benzoic Acid (DSP-103; 103)

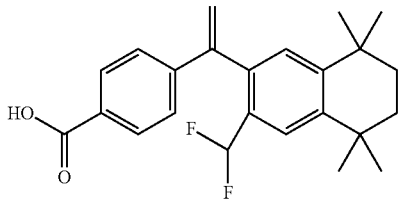

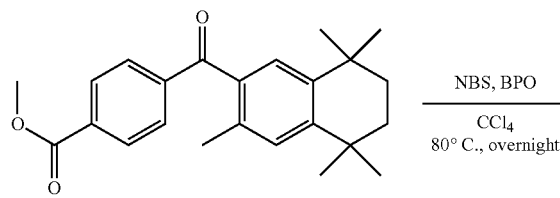

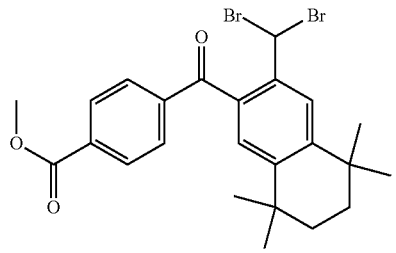

A solution of 4-[(3,5,5,8,8-pentamethyl-5,6,7,8-tetrahydronaphthalen-2-yl)carbonyl]benzoate (1 g, 2.7 mmol, 1.0 eq.), NBS (3.81 g, 21.9 mmol, 8.0 eq.), and benzoyl peroxide (200 mg, 0.83 mmol, 0.30 eq.) in CCl$_4$ (20 mL) was heated at 80° C. overnight. The reaction mixture was cooled to room temperature, then quenched by the addition of H$_2$O (20 mL). The resulting mixture was extracted with CH$_2$Cl$_2$ (2×20 mL), then the combined organic layers were washed with brine, dried (Na$_2$SO$_4$), and concentrated under reduced pressured. The residue was purified by silica gel chromatography eluting with EtOAc/petroleum ether (1:50) to give 1 g of crude methyl 4-[[3-(dibromomethyl)-5,5,8,8-tetramethyl-5,6,7,8-tetrahydronaphthalen-2-yl]carbonyl]benzoate as a brown solid.

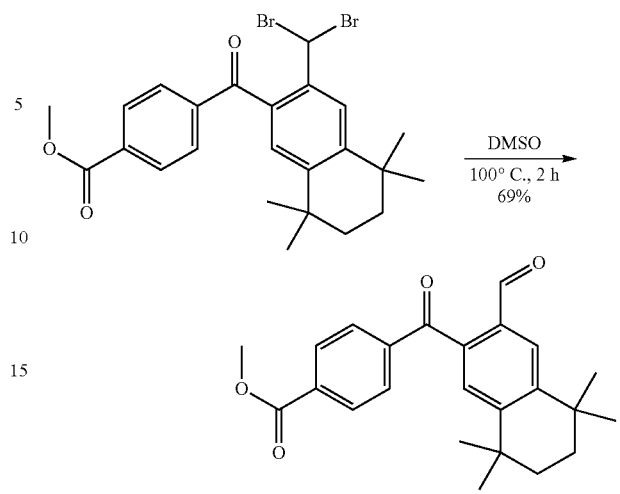

A solution of 4-[[3-(dibromomethyl)-5,5,8,8-tetramethyl-5,6,7,8-tetrahydronaphthalen-2-yl]carbonyl]benzoate (1 g, 1.9 mmol, 1.0 eq.) in DMSO (20 mL) was heated at 100° C. for 2 h, then the reaction mixture was cooled to room temperature. The resulting solution was diluted with H$_2$O (20 mL) then extracted with EtOAc (3×20 mL). The combined organic layers were washed with brine, dried (Na$_2$SO$_4$), and concentrated under reduced pressure. The residue was purified by silica gel chromatography eluting with EtOAc/petroleum ether (1:20) to give 500 mg (69%) of methyl 4-[(3-formyl-5,5,8,8-tetramethyl-5,6,7,8-tetrahydronaphthalen-2-yl)carbonyl]benzoate as a white solid.

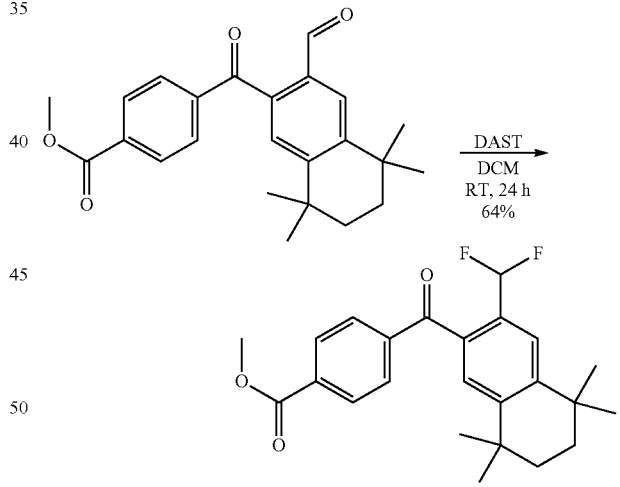

A solution of methyl 4-[(3-formyl-5,5,8,8-tetramethyl-5,6,7,8-tetrahydronaphthalen-2-yl)carbonyl]benzoate (500 mg, 1.3 mmol, 1.0 eq.) and diethylaminosulfur trifluoride (1.28 g, 7.9 mmol, 6.0 eq.) in CH$_2$Cl$_2$ (5 mL) was stirred at room temperature for 24 hours, then cooled to 0° C. and quenched by the addition of H$_2$O (20 mL). The resulting solution was extracted with CH$_2$Cl$_2$ (3×20 mL), then the combined extracts were washed with brine, dried (Na$_2$SO$_4$), and concentrated under reduced pressure. The residue was purified by silica gel chromatography eluting with petroleum ether to give 340 mg (64%) of methyl 4-[[3-(difluoromethyl)-5,5,8,8-tetramethyl-5,6,7,8-tetrahydronaphthalen-2-yl]carbonyl]benzoate as a light-yellow solid.

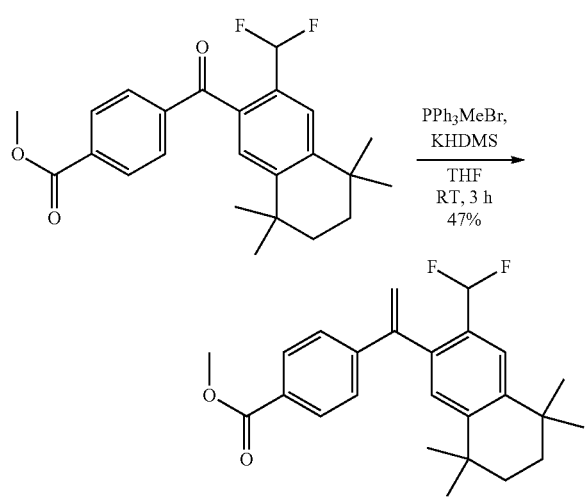

To a solution of Ph₃PMeBr (802 mg, 2.3 mmol, 3.0 eq.) in THF (10 mL) at −30° C. was added a solution of potassium hexamethyldisilazide in THF (1 M, 2.6 mL, 2.6 mmol, 3.5 eq.) in a dropwise fashion. The resulting solution was stirred at 0° C. for 40 minutes, cooled to −30° C., and then a solution of methyl 4-[[3-(difluoromethyl)-5,5,8,8-tetramethyl-5,6,7,8-tetrahydronaphthalen-2-yl]carbonyl]benzoate (300 mg, 0.75 mmol, 1.0 eq.) in THF (10 mL) was added in a dropwise fashion. The resulting solution was stirred at room temperature for 3 h, cooled to 0° C., then quenched by the addition of H₂O (20 mL). The resulting mixture was extracted with EtOAc (2×20 mL), then the combined extracts were washed with brine, dried (Na₂SO₄), and concentrated under reduced pressure. The residue was purified by silica gel chromatography eluting with EtOAc/petroleum ether (0/1-1/50) to give 140 mg (47%) of methyl 4-[1-[3-(difluoromethyl)-5,5,8,8-tetramethyl-5,6,7,8-tetrahydronaphthalen-2-yl]ethenyl]benzoate as a light-yellow solid.

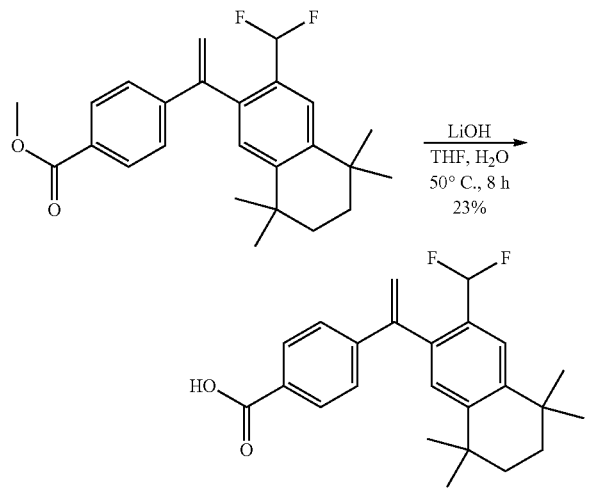

A mixture of methyl 4-[1-[3-(difluoromethyl)-5,5,8,8-tetramethyl-5,6,7,8-tetrahydronaphthalen-2-yl]ethenyl]benzoate (140 mg, 0.35 mmol, 1.0 eq.) and lithium hydroxide (84 mg, 3.5 mmol, 10.0 eq.) in THF (6 mL) and H₂O (6 mL) was stirred at 50° C. for 8 h, then cooled to 0° C. and the pH of the solution was adjusted to 5-6 by the action of HCl (1 M). The resulting mixture was extracted with EtOAc (3×20 mL), and the combined organic layers were washed with brine, dried (Na₂SO₄), and concentrated under reduced pressure. The residue was purified by Flash-Prep-HPLC with the following conditions (IntelFlash-1): C18 Column; mobile phase, 40% methanol/water (containing 0.05% formic acid) to 100% methanol (containing 0.05% formic acid) over 15 min; Detector, UV 254 nm. Removal of the solvents gave 31 mg (23%) of 4-[1-[3-(difluoromethyl)-5,5,8,8-tetramethyl-5,6,7,8-tetrahydronaphthalen-2-yl]ethenyl]benzoic acid as a white solid: ¹H-NMR (300 MHz, CDCl₃, ppm): δ 8.07 (d, J=8.4 Hz, 2H), 7.67 (s, 1H), 7.40 (d, J=8.4 Hz, 2H), 7.15 (s, 1H), 6.51 (t, J=55.5 Hz, 1H), 6.00 (s, 1H), 5.42 (s, 1H), 1.75 (s, 4H), 1.37 (s, 6H), 1.28 (s, 6H). LC-MS: (ES, m/z): [M+H]=385.

Example 5: Preparation of 4-(1-(6'-chloro-4',4'-dimethyl-3',4'-dihydro-2'H-spiro[cyclopropane-1,1'-naphthalen]-7'-yl)vinyl)benzoic Acid (DSP-108; 108)

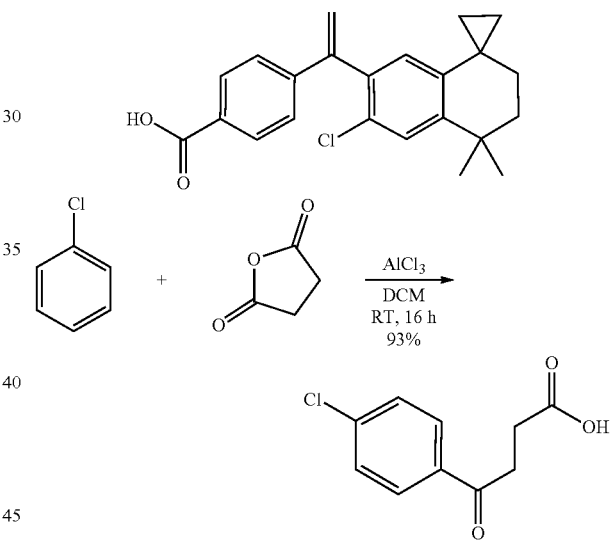

A mixture of chlorobenzene (50 g, 444 mmol, 1.2 eq.), oxolane-2,5-dione (44.4 g, 444 mmol, 1.0 eq.) and aluminum trichloride (74.01 g, 555 mmol, 1.5 eq.) in CH₂Cl₂ (500 mL) was stirred at room temperature for 16 h, then quenched by the addition of 1 M HCl/ice (600 mL). The resulting mixture was extracted with diethyl ether (3×300 mL), then the combined extracts were dried (Na₂SO₄) and concentrated under reduced pressure to give 73 g (93%) of 4-(4-chlorophenyl)-4-oxobutanoic acid as a white solid.

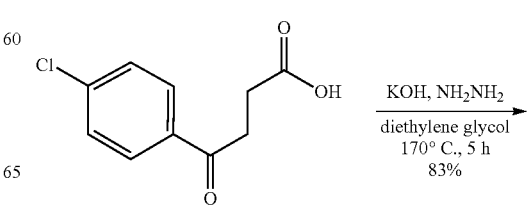

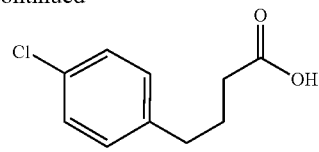

A solution of 4-(4-chlorophenyl)-4-oxobutanoic acid (50 g, 235 mmol, 1.0 eq.), hydrazine (9.78 g, 305 mmol, 1.3 eq.) and potassium hydroxide (34 g, 606 mmol, 2.6 eq.) in diethylene glycol (250 mL) was heated at 170° C. for 5 h, then cooled to room temperature and quenched by the addition of aqueous HCl (200 mL). The resulting solution was diluted with $H_2O$ (100 mL) and the pH of the solution was adjusted to 12 by the action of sodium hydroxide (2 M). The resulting mixture was extracted with $CH_2Cl_2$ (3×200 mL), then the combined organic layers were dried ($Na_2SO_4$) and concentrated to give 39 g (83%) of 4-(4-chlorophenyl) butanoic acid as a yellow solid.

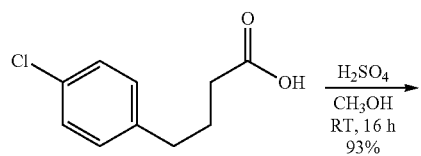

A solution of 4-(4-chlorophenyl)butanoic acid (36 g, 181 mmol, 1.0 eq.) and concentrated sulfuric acid (36 mL) in methanol (360 mL) was stirred at room temperature for 16 hours, then concentrated under reduced pressure. The residue was taken up in EtOAc and then washed with $H_2O$ (2×100 mL), saturated aqueous $NaHCO_3$ (100 mL) and brine. The organic layer was dried ($MgSO_4$) and concentrated under reduced pressure to give 36 g (93%) of methyl 4-(4-chlorophenyl)butanoate as a white solid.

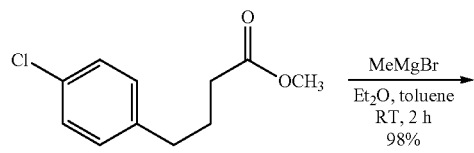

To a solution of methyl 4-(4-chlorophenyl)butanoate (36.5 g, 172 mmol, 1.0 eq.) in diethyl ether (292 mL) and toluene (580 mL) at 0° C. was added MeMgBr (49.2 g, 413 mmol, 2.4 eq.) in several batches over 30 minutes. The resulting solution was stirred at 30° C. for 2 h, whereupon saturated ammonium chloride (100 mL) was added, then the pH of the solution was adjusted to 7 by the action of HCl (2 M). The resulting mixture was extracted with EtOAc (2×200 mL), then the combined extracts were washed with brine, dried ($Na_2SO_4$), and concentrated under reduced pressure to give 35.7 g (98%) of 5-(4-chlorophenyl)-2-methylpentan-2-ol as yellow oil.

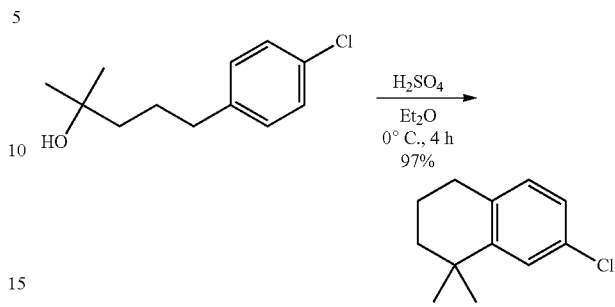

To a solution of 5-(4-chlorophenyl)-2-methylpentan-2-ol (35 g, 164.5 mmol, 1.0 eq.) in diethyl ether (175 mL) at 0° C. was added sulfuric acid (105 mL) in a dropwise fashion. The reaction mixture was stirred at 0° C. for 4 h, whereupon the solution was diluted with $H_2O$ (100 mL). The mixture was extracted with diethyl ether (3×100 mL), then the combined organic layers were washed with saturated aqueous $NaHCO_3$ (2×100 mL) and concentrated under reduced pressure to give 31 g (97%) of 7-chloro-1,1-dimethyl-1,2,3,4-tetrahydronaphthalene as a yellow oil.

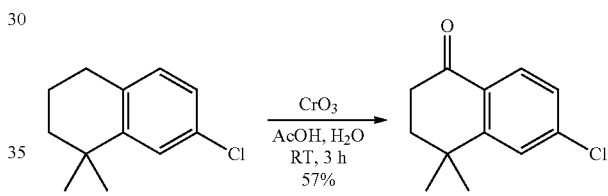

To a solution of 7-chloro-1,1-dimethyl-1,2,3,4-tetrahydronaphthalene (15 g, 77.0 mmol, 1.0 eq.) in acetic acid (225 mL) at 0° C. was added a solution of chromium trioxide (35.4 g, 354 mmol, 5.0 eq.) in $H_2O$ (225 mL) in a dropwise fashion over 30 minutes. The resulting solution was stirred at room temperature for 3 h, whereupon i-propanol (100 mL) was added. The mixture was washed with saturated aqueous $NaHCO_3$ (2×100 mL), then brine. The resulting solution was extracted with EtOAc (3×200 mL), then the combined organic layers were dried ($Na_2SO_4$) and concentrated under reduced pressure to give 9.1 g (57%) of 6-chloro-4,4-dimethyl-1,2,3,4-tetrahydronaphthalen-1-one as yellow oil.

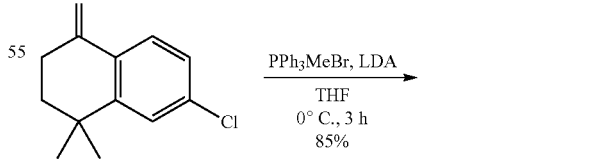

To a solution of PPh₃MeBr (39.4 g, 110.3 mmol, 3.0 eq.) in THF (450 mL) at −10° C. was added a solution of LDA in THF (1 M, 65 mL, 130 mmol, 3.0 eq.) in a dropwise fashion over 20 minutes. To the mixture was added 6-chloro-4,4-dimethyl-1,2,3,4-tetrahydronaphthalen-1-one (9 g, 43.1 mmol, 1.0 eq.) in THF (50 mL), then the resulting solution was stirred at 0° C. for 3 h. The reaction mixture was quenched by the addition of ice/H₂O (40 mL), then the mixture was extracted with EtOAc (3×100 mL). The combined organic layers were dried (Na₂SO₄) and concentrated under reduced pressure. The residue was purified by silica gel chromatography eluting with petroleum ether to give 7.6 g (85%) of 7-chloro-1,1-dimethyl-4-methylidene-1,2,3,4-tetrahydronaphthalene as colorless oil.

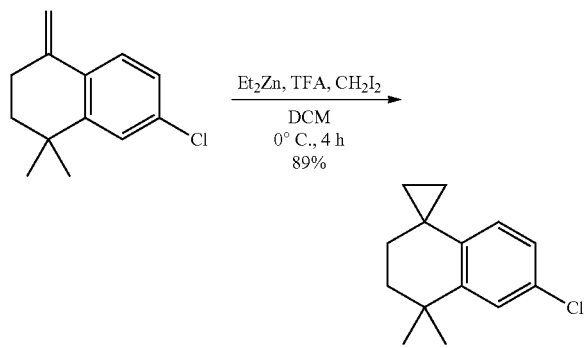

To a mixture of diethylzinc (47.7 g, 387 mmol, 10.0 eq.) in CH₂Cl₂ (288 mL) at 0° C. was added trifluoroacetic acid (38 g, 387 mmol, 10.0 eq.) in a dropwise fashion over 20 minutes. The mixture was stirred at 0° C. for 1 h, then diiodomethane (103.9 g, 387 mmol, 10.0 eq.) was added in a dropwise fashion over 20 minutes. The resulting mixture was stirred for at 0° C. for 1 h, then a solution of 7-chloro-1,1-dimethyl-4-methylidene-1,2,3,4-tetrahydronaphthalene (8 g, 38.7 mmol, 1.0 eq.) in CH₂Cl₂ (20 mL) was added. The resulting solution was stirred at 0° C. for 4 h, then quenched by the addition of saturated aqueous NaHCO₃ (100 mL) was added. The mixture was extracted with CH₂Cl₂ (3×200 mL), then the combined organic layers were combined, dried (Na₂SO₄) and concentrated under reduced pressure to give 7.6 g (89%) of 6-chloro-4,4-dimethyl-3,4-dihydro-2H-spiro[cyclopropane-1,1-naphthalene] as colorless oil.

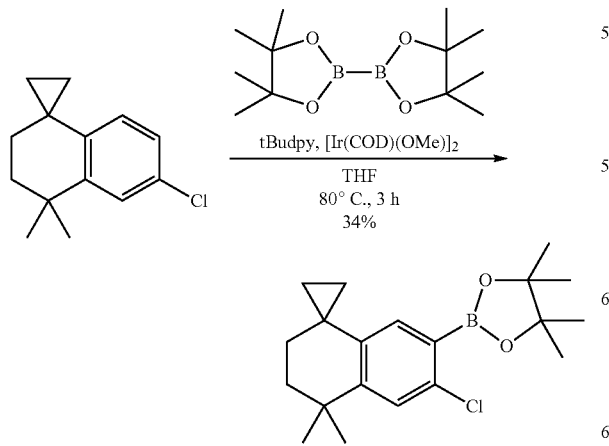

A mixture of 6-chloro-4,4-dimethyl-3,4-dihydro-2H-spiro[cyclopropane-1,1-naphthalene] (1 g, 4.5 mmol, 1.0 eq.) and 4,4,5,5-tetramethyl-2-(tetramethyl-1,3,2-dioxaborolan-2-yl)-1,3,2-dioxaborolane (1.73 g, 6.8 mmol, 1.50 eq.) in THF (25 mL) was degassed 3 times with a nitrogen sparge, then t-Budpy (123 mg, 0.60 mmol, 0.10 eq.) and bis(methoxyiridiumcarbaldehyde) (150 mg, 0.30 mmol, 0.05 eq.) were added and the resulting mixture was heated at 80° C. for 3 hours. The reaction mixture was cooled to room temperature, then purified by Prep-HPLC with the following conditions: Column, C₁₈; mobile phase, ACN/H₂O, 70%-90% within 30 min; Detector, UV 210 nm. Removal of the solvents gave 530 mg (34%) of 2-(6-chloro-4,4-dimethyl-3,4-dihydro-2H-spiro[cyclopropane-1,1-naphthalen]-7-yl)-4,4,5,5-tetramethyl-1,3,2-dioxaborolane as a white solid.

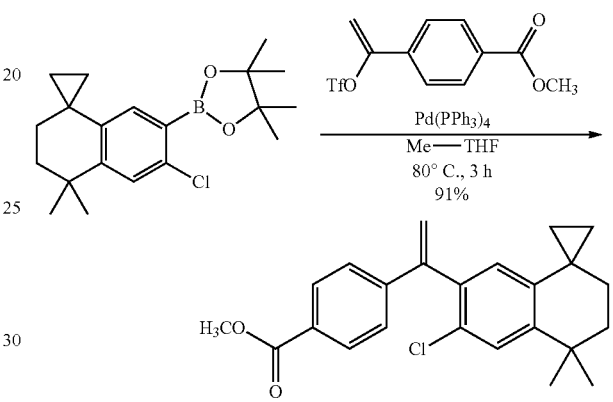

A mixture of methyl 4-[1-[(trifluoromethane)sulfonyloxy]ethenyl]benzoate (522 mg, 1.68 mmol, 1.10 eq.), 2-(6-chloro-4,4-dimethyl-3,4-dihydro-2H-spiro[cyclopropane-1,1-naphthalen]-7-yl)-4,4,5,5-tetramethyl-1,3,2-dioxaborolane (500 mg, 1.44 mmol, 1.0 eq.), and K₃PO₄ (974 mg, 4.59 mmol, 3.0 eq.) in 2-Me THF (15 mL) was degassed 3 times by nitrogen sparge, then tetrakis(triphenylphosphane) palladium (177 mg, 0.15 mmol, 0.11 eq.) was added and the resulting solution was stirred at 80° C. for 3 hours. The crude product (10 mL) was purified by Prep-HPLC with the following conditions: Column, C18; mobile phase, ACN/H₂O, 70%-90% over 30 minutes; Detector, UV 210 nm. Removal of the solvents gave 500 mg (91%) of methyl 4-(1-(6-chloro-4,4-dimethyl-3,4-dihydro-2H-spiro[cyclopropane-1,1-naphthalen]-7-yl)vinyl)benzoate as a white solid.

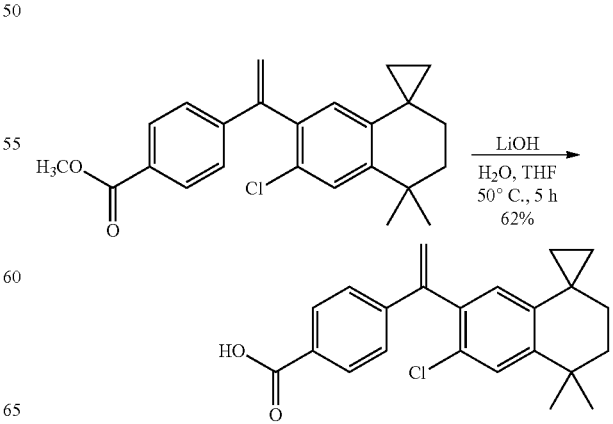

A mixture of methyl 4-(1-[6-chloro-4,4-dimethyl-3,4-dihydro-2H-spiro[cyclopropane-1,1-naphthalene]-7-yl]ethenyl)benzoate (500 mg, 1.3 mmol, 1.0 eq.), water (1 mL), and lithium hydroxide (63 mg, 2.6 mmol, 2.0 eq.) in THF (15 mL) was stirred at 50° C. for 5 h, then cooled to room temperature. The pH of the solution was adjusted to 2 by the action of 2 M HCl, then the mixture was washed with H₂O (2×10 mL) and diethyl ether (3×10 mL), then concentrated to give 300 mg (62%) of 4-(1-[6-chloro-4,4-dimethyl-3,4-dihydro-2H-spiro[cyclopropane-1,1-naphthalene]-7-yl]ethenyl)benzoic acid as an off-white solid: ¹H-NMR: (400 MHz, DMSO, ppm): δ 12.93 (s, 1H), 7.89 (d, J=8.4 Hz, 2H), 7.40 (s, 1H), 7.32 (d, J=8.4 Hz, 2H), 6.61 (s, 1H), 5.97 (s, 1H), 5.36 (s, 1H), 1.74 (t, J=4.8 Hz, 2H), 1.66 (t, J=4.8 Hz, 2H), 1.31 (s, 6H), 0.96 (t, J=4.8 Hz, 2H), 0.83 (t, J=4.8 Hz, 2H). LC-MS: (ES, m/z): 367 [M+H]⁺, 365 [M−H]⁻.

Example 6: Preparation of 4-(1-(3,5,5,8,8-pentamethyl-5,6,7,8-tetrahydronaphthalen-2-yl)cyclopropyl) benzoic Acid (DSP-105; 105)

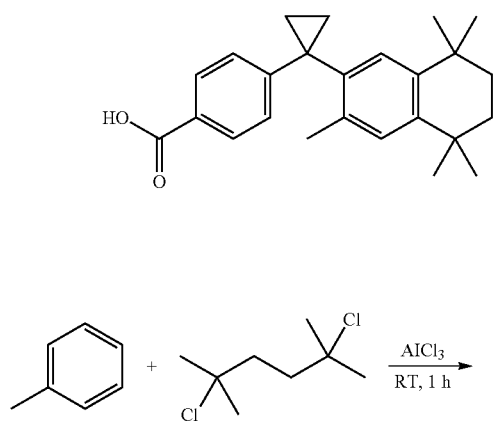

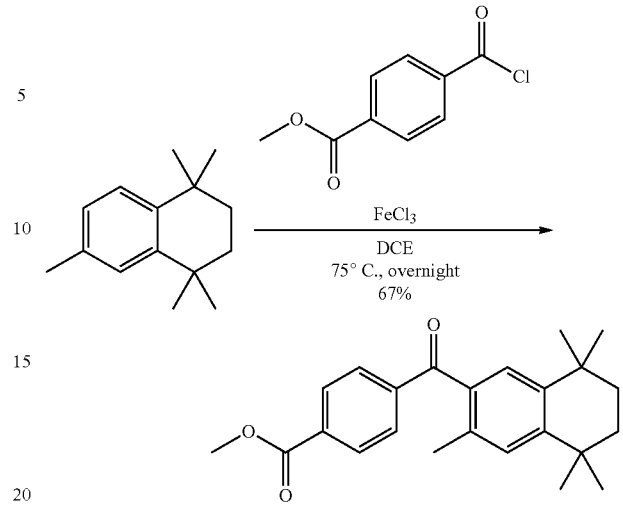

Into a 25-mL round-bottom flask purged and maintained with an inert atmosphere of nitrogen, was placed 1,1,4,4,6-pentamethyl-1,2,3,4-tetrahydronaphthalene (6.6 g, 32.62 mmol, 1.00 equiv), DCE (70 mL), methyl 4-(carbonochloridoyl)benzoate (6.5 g, 32.62 mmol, 1.00 eq.), FeCl₃ (300 mg, 1.63 mmol, 0.05 eq.). The resulting solution was stirred overnight at 75° C. in an oil bath. The reaction mixture was cooled to room temperature. The reaction was then quenched by the addition of 70 mL of water. The resulting solution was extracted with 2×70 mL of DCM and the organic layers combined. The resulting mixture was washed with 1×100 mL of brine and dried over anhydrous sodium sulfate and concentrated under vacuum. The crude product was re-crystallized from methanol. This resulted in 8 g (67%) of methyl 4-[(3,5,5,8,8-pentamethyl-5,6,7,8-tetrahydronaphthalen-2-yl)carbonyl]benzoate as a gray solid.

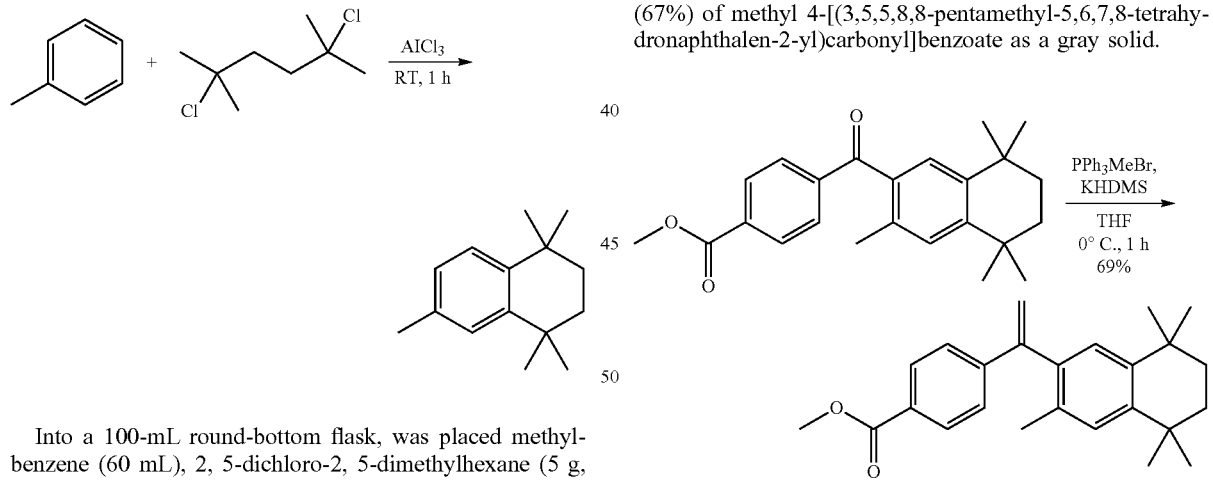

Into a 100-mL round-bottom flask, was placed methylbenzene (60 mL), 2,5-dichloro-2,5-dimethylhexane (5 g, 27.30 mmol, 1.00 eq.). This was followed by the addition of AlCl₃ (2.7 g, 20.48 mmol, 0.75 eq.) in several portions at 0° C. The resulting solution was stirred for 1 h at room temperature. The reaction mixture was cooled to 0° C. The reaction was then quenched by the addition of 30 mL of water. The resulting solution was extracted with 2×50 mL of ethyl acetate and the organic layers combined. The resulting mixture was washed with 1×50 mL of brine and dried over anhydrous sodium sulfate and concentrated under vacuum. The residue was applied onto a silica gel column with EtOAc/petroleum ether (1/5). This resulted in 6.6 g (crude) of 1,1,4,4,6-pentamethyl-1,2,3,4-tetrahydronaphthalene as light yellow oil.

Into a 50-mL round-bottom flask purged and maintained with an inert atmosphere of nitrogen, was placed PPh₃MeBr (1715 mg, 4.80 mmol, 2.50 eq.), THF (10 mL). This was followed by the addition of KHDMS (1 M) (5.1 mL, 5.11 mmol, 2.66 eq.) dropwise with stirring at −30° C. The resulting solution was stirred for 30 min at 0° C. To this was added a solution of methyl 4-[(3,5,5,8,8-pentamethyl-5,6,7,8-tetrahydronaphthalen-2-yl)carbonyl]benzoate (700 mg, 1.92 mmol, 1.00 eq.) in THF (7 mL) dropwise with stirring at −30° C. The resulting solution was stirred for 1 h at 0° C. The reaction was then quenched by the addition of 20 mL of water at 0° C. The resulting solution was extracted with 2×20 mL of ethyl acetate and the organic layers combined. The resulting mixture was washed with 1×20 mL of brine. The mixture was dried over anhydrous sodium sulfate and concentrated under vacuum. The residue was applied onto a silica gel column with ethyl acetate/petroleum ether (1/10). This resulted in 480 mg (69%) of methyl 4-[1-(3,5,5,8,8-pentamethyl-5,6,7,8-tetrahydronaphthalen-2-yl)ethenyl]benzoate as a light yellow solid.

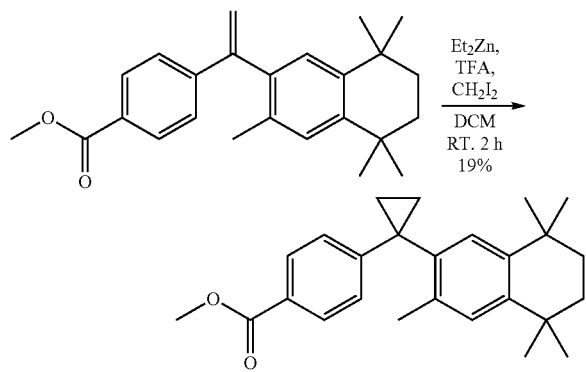

Into a 50-mL round-bottom flask purged and maintained with an inert atmosphere of nitrogen, was placed Et₂Zn (1M) (1.4 mL, 1.4 mmol, 10.00 eq.), DCM (2 mL). This was followed by the addition of TFA (157 mg, 1.39 mmol, 10.00 eq.) dropwise with stirring at 0° C. The resulting solution was stirred for 30 min at 0° C. To this was added CH₂I₂ (370 mg, 1.4 mmol, 10.00 equiv) dropwise with stirring at 0° C. The resulting solution was stirred for 30 min at 0° C. To the mixture was added a solution of methyl 4-[1-(3,5,5,8,8-pentamethyl-5,6,7,8-tetrahydronaphthalen-2-yl)ethenyl]benzoate (50 mg, 0.14 mmol, 1.00 equiv) in DCM (1 mL) dropwise with stirring at 0° C. The resulting solution was stirred for 2 h at room temperature. The reaction was then quenched by the addition of 20 mL of water at 0° C. The solid was filtered out. The resulting solution was extracted with 2×20 mL of dichloromethane and the organic layers combined. The resulting mixture was washed with 1×20 ml of brine and dried over anhydrous sodium sulfate and concentrated under vacuum. The residue was applied onto a silica gel column with ethyl acetate/petroleum ether (1/10). This resulted in 10 mg (19%) of methyl 4-[1-(3,5,5,8,8-pentamethyl-5,6,7,8-tetrahydronaphthalen-2-yl)cyclopropyl]benzoate as a white solid.

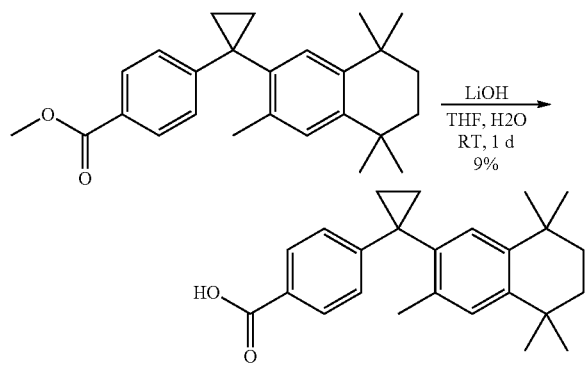

Into a 50-mL round-bottom flask, was placed methyl 4-[1-(3,5,5,8,8-pentamethyl-5,6,7,8-tetrahydronaphthalen-2-yl)cyclopropyl]benzoate (330 mg, 0.88 mmol, 1.00 equiv), THF (6 mL), water (6 mL), LiOH (210 mg, 8.77 mmol, 10.00 equiv). The resulting solution was stirred for 1 day at 50° C. The reaction mixture was cooled to room temperature and concentrated under vacuum. The pH value of the solution was adjusted to 3 with hydrogen chloride (1 mol/L) at 0° C. The solids were collected by filtration. The crude product was purified by Flash-Prep-HPLC with the following conditions (Intel Flash-1): column, C18, Mobile phase, ACN/water=0 increasing to ACN/water=100 in 30 min; Detector: UV 254 nm. This resulted in 30 mg (9%) of 4-(1-(3,5,5,8,8-pentamethyl-5,6,7,8-tetrahydronaphthalen-2-yl)cyclopropyl)benzoic acid as a white solid. $^1$H-NMR: (300 Hz, CDCl₃, ppm): δ 7.86 (d, J=8.4 Hz, 2H), 7.33 (s, 1H), 7.13 (s, 1H), 6.98 (d, J=8.4 Hz, 2H), 2.13 (s, 3H), 1.73 (s, 4H), 1.47-1.44 (m, 2H), 1.36-1.34 (m, 2H), 1.31 (d, J=1.8 Hz, 12H). LC-MS: (ES, m/z): [M+H]=363.

Example 7: Activity in HL60 Cells

HL60 cells were grown in RPMI, 10% fetal bovine serum and plated at a density of 0.5×10⁶ cells/mL in the presence of compound of the disclosure, all-trans retinoic acid (ATRA) (positive control), or DMSO (negative control) for 24 hours. Cells were washed and blocked with rabbit serum prior to staining. Mouse anti-human CD45 BV711 and CD38 PE-Cy7 in the presence of FVS510 (BD Biosciences, San Jose, CA, USA) were used to measure CD38 induction as an indication of cell differentiation. Data was acquired on a BD LSR II flow cytometer using Diva software (BD Biosciences). Flow plots were analyzed using FlowJo (V10) and FCS Express (6.06.0014). CD38 induction is shown as a percentage of total cells after gating for singlet exclusion (FSC-H/FSC-A) and viability (FVS510-). The results are presented in FIG. 1. The compounds of the disclosure induce dose dependent CD38 expression in HL60 cells, suggesting early stage differentiation of leukemic blasts.

Example 8: Activity in MV4;11 Cells

Figure 2:
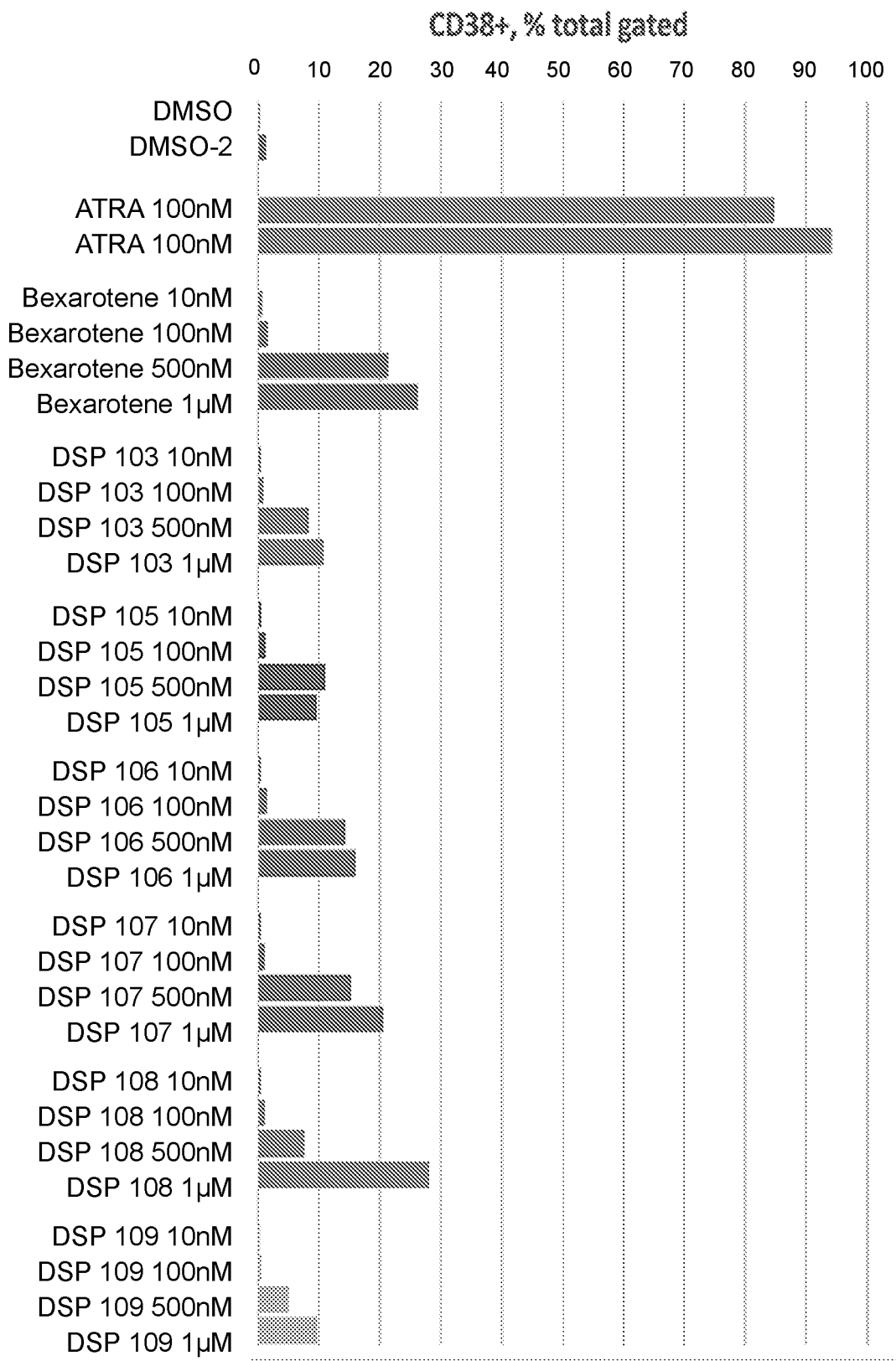
FIG. 2 illustrates the activity of the compounds of the disclosure in dose dependent CD38 expression in MV4;11 (human biphenotypic B myelomonocytic leukemia) cells.

MV4;11 cells were grown in RPMI, 10% fetal bovine serum and plated at a density of 0.5*106 cells/mL in the presence of compound of the disclosure, ATRA (positive control), or DMSO (negative control) for 24 hours. Cells were washed and blocked with rabbit serum prior to staining. Mouse anti-human CD45 BV711 and CD38 PE-Cy7 in the presence of FVS510 (BD Biosciences, San Jose, CA, USA) were used to measure CD38 induction as an indication of cell differentiation. Data was acquired on a BD LSR II flow cytometer using Diva software (BD Biosciences). Flow plots were analyzed using FlowJo (V10) and FCS Express (6.06.0014). CD38 induction is shown as a percentage of total cells after gating for singlet exclusion (FSC-H/FSC-A) and viability (FVS510-). The results are presented in FIG. 2. The compounds of the disclosure induce dose dependent CD38 expression in MV4;11 cells, suggesting early stage differentiation of leukemic blasts.

Example 9: Activity in NB4 Cells

Figure 3:
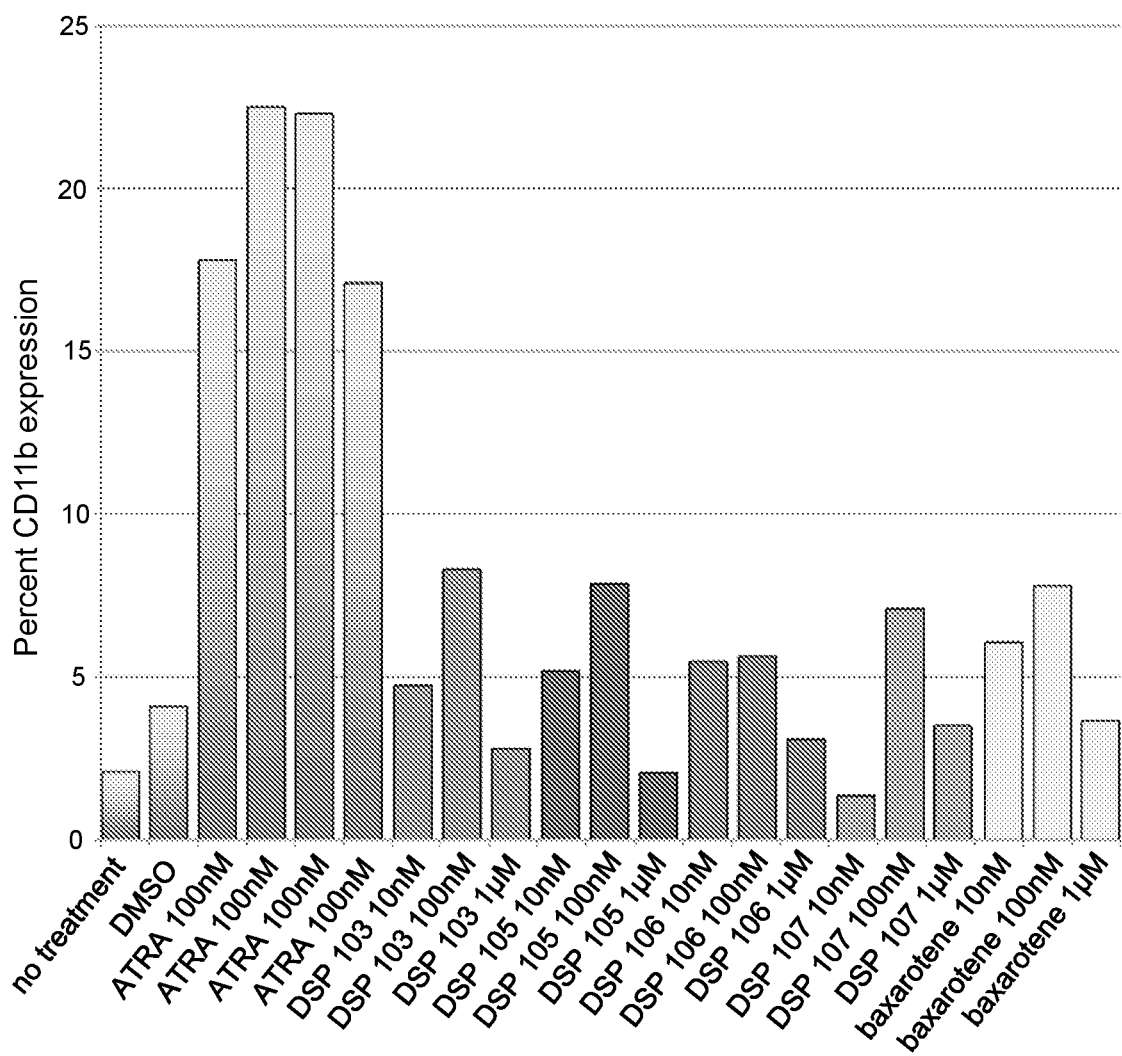
FIG. 3 illustrates the activity of the compounds of the disclosure in dose dependent CD11 b expression in NB4 (human acute promyelocytic leukemia) cells.

NB4 cells were grown in RPMI, 10% fetal bovine serum and plated at a density of 25000 cells/ml in presence of compound of the disclosure, ATRA (positive control), or DMSO (negative control) for 4 days. Cells were washed and blocked with rabbit serum prior to staining. Mouse anti-human CD11 b PE and Live-Dead Aqua (BD Biosciences, San Jose, CA, USA) were used to measure CD11 b induction as an indication of cell differentiation. Data was acquired on a BD LSR II flow cytometer using Diva software (BD Biosciences). Flow plots were analyzed using FlowJo (V10) and FCS Express (6.06.0014). CD38 induction is shown as a percentage of total cells after gating for singlet exclusion (FSC-H/FSC-A) and viability (FVS510-). ATRA positive control was run repeated ×4. The results are presented in FIG. 3. The compounds of the disclosure and bexarotene show similar levels of late stage differentiation activity and dose response patterns.

Example 10: Cell Count Activity

Figure 4:
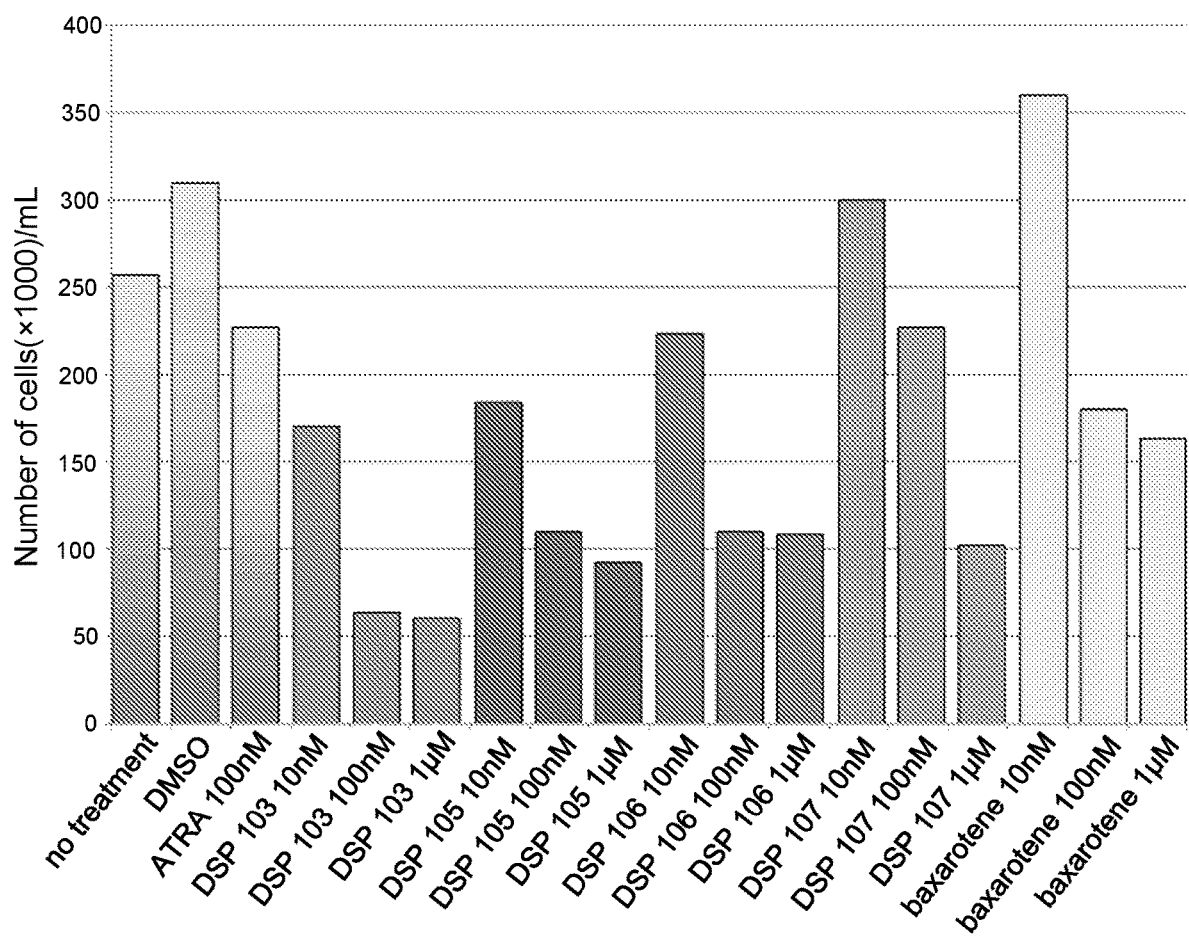
FIG. 4 illustrates the cell count in NB4 cells after the incubation with the compounds of the disclosure.
Figure 5:
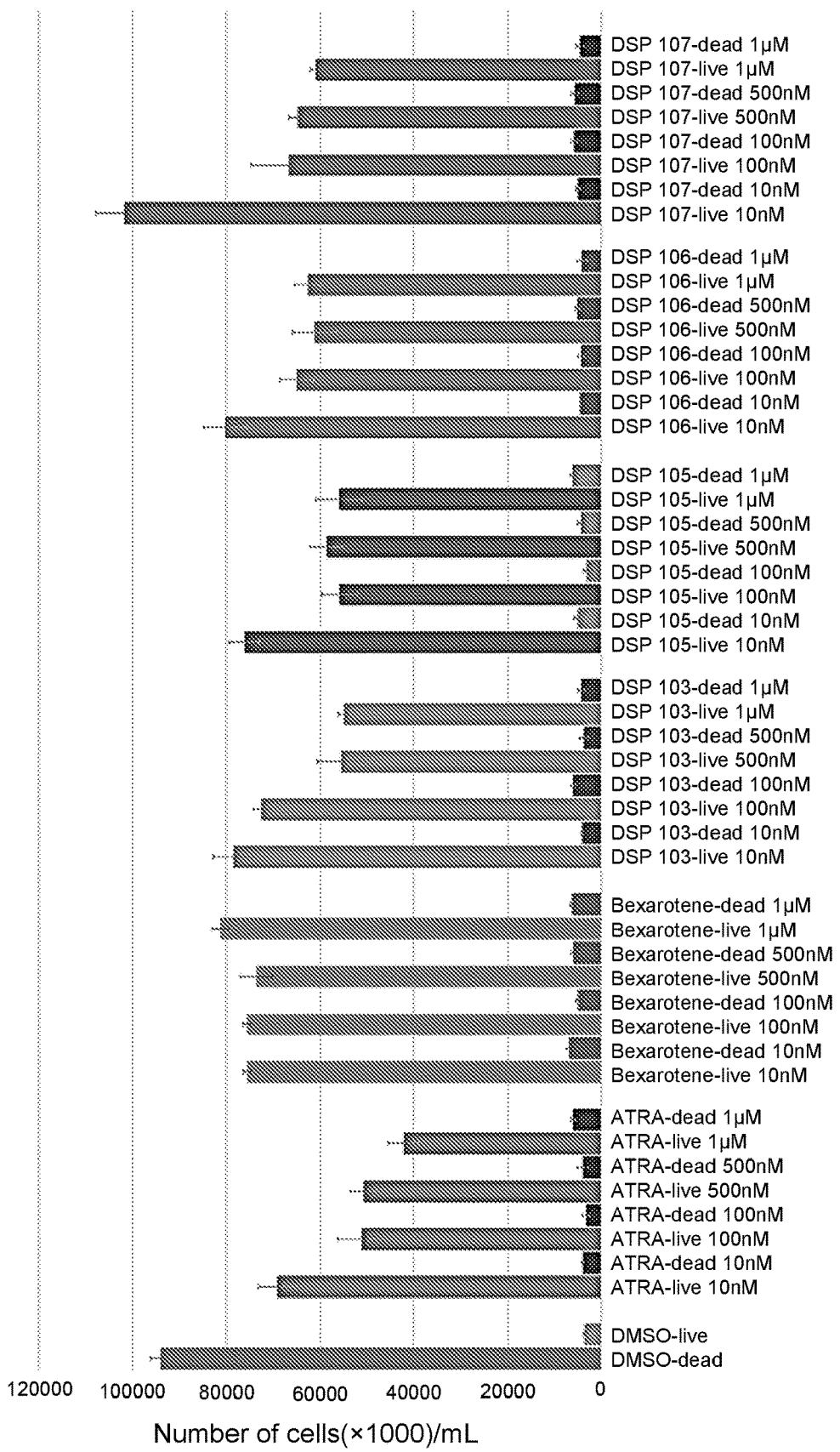
FIG. 5 illustrates the cell count in MV4;11 cells after the incubation with the compounds of the disclosure.

NB4 cells or MV4;11 cells were grown in RPMI, 10% fetal bovine serum and plated at a density of 25,000 cells/mL in presence or absence of compound of the disclosure (dissolved in DMSO) for 5 days. Cells were counted manually on a light microscope using a hemocytometer and Trypan blue exclusion or on the Nexcelom Cellometer Auto 2000 using Cellometer Viastain AOPI staining solution (Nexcelom CS2-0106). FIG. 4 illustrates that NB4 cells show dose dependent reduction in cell counts after incubation with the compounds of the disclosure or bexarotene, with reduction in cell counts with the compounds of the disclosure appearing greater than that seen with comparable levels of bexarotene. FIG. 5 illustrates that MV4;11 cells show dose dependent reduction in cell counts when incubated with the compounds of the disclosure or ATRA, with the compounds of the disclosure showing greater cell count reductions than similar doses of bexarotene.

Various aspects of the disclosure are further exemplified by the non-limiting embodiments recited in the claims below. In each case, features of multiple claims can be combined in any fashion not inconsistent with the specification and not logically inconsistent.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A compound of formula:

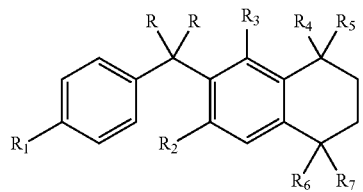

or pharmaceutically acceptable salts thereof, wherein
two R groups and the carbon atom to which they are attached form =$CH_2$ or cyclopropyl ring;
$R_1$ is —$CO_2H$;
$R_2$ is halogen or methyl;
$R_3$ is halogen;
$R_4$ and $R_5$ are independently $C_1$-$C_6$ alkyl or $C_1$-$C_6$ haloalkyl, or $R_4$ and $R_5$ are together with the carbon atoms to which they are attached form $C_3$ cycloalkyl optionally substituted with one or more $R_8$;
$R_6$ and $R_7$ are independently $C_1$-$C_6$ alkyl or $C_1$-$C_6$ haloalkyl, or $R_6$ and $R_7$ are together with the carbon atoms to which they are attached form $C_3$ cycloalkyl optionally substituted with one or more $R_8$;
wherein each $R_8$ is independently halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, or $C_1$-$C_6$ haloalkoxy.

2. The compound of claim 1, wherein two R groups and the carbon atom to which they are attached form =$CH_2$.

3. The compound of claim 1, wherein two R groups and the carbon atom to which they are attached form cyclopropyl ring.

4. The compound of claim 1, wherein $R_2$ is halogen.

5. The compound of claim 1, wherein $R_3$ is fluoro.

6. The compound of claim 1, wherein $R_4$ and $R_5$ are together with the carbon atoms to which they are attached form cyclopropyl optionally substituted with one or more $R_8$; or $R_4$ and $R_5$ are together with the carbon atoms to which they are attached form unsubstituted cyclopropyl.

7. The compound of claim 1, wherein $R_4$ and $R_5$ are independently $C_1$-$C_6$ alkyl; or $R_4$ and $R_5$ are independently methyl.

8. The compound of claim 1, wherein $R_6$ and $R_7$ are together with the carbon atoms to which they are attached form cyclopropyl optionally substituted with one or more $R_8$; or $R_6$ and $R_7$ are together with the carbon atoms to which they are attached form unsubstituted cyclopropyl.

9. The compound of claim 1, wherein $R_6$ and $R_7$ are independently $C_1$-$C_6$ alkyl; or $R_6$ and $R_7$ are independently methyl.

10. The compound of claim 1, wherein $R_4$ and $R_5$ together with the carbon atoms to which they are attached form $C_3$ cycloalkyl optionally substituted with one or more $R_8$; and $R_6$ and $R_7$ are independently $C_1$-$C_6$ alkyl or $C_1$-$C_6$ haloalkyl.

11. The compound of claim 1, selected from the following group:

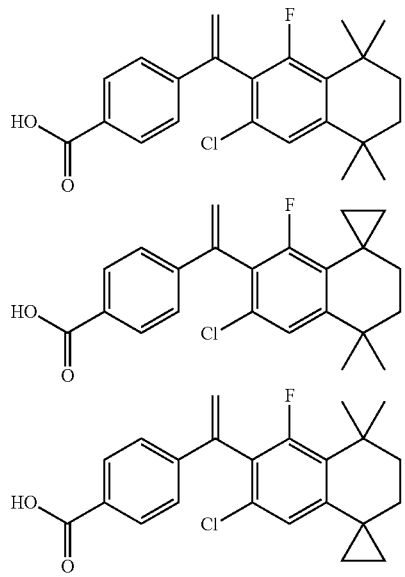

-continued

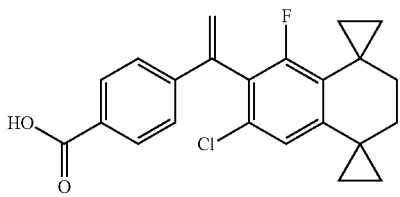

and pharmaceutically acceptable salts thereof.

12. The compound of claim 1, selected from:

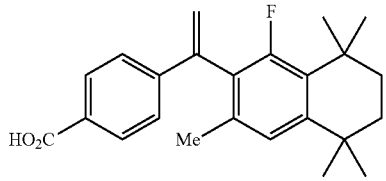 [SMILES: C=C(c1ccc(C(=O)O)cc1)c1c(C)cc2c(c1F)C(C)(C)CCC2(C)C]

and pharmaceutically acceptable salts thereof.

13. A compound having the formula:

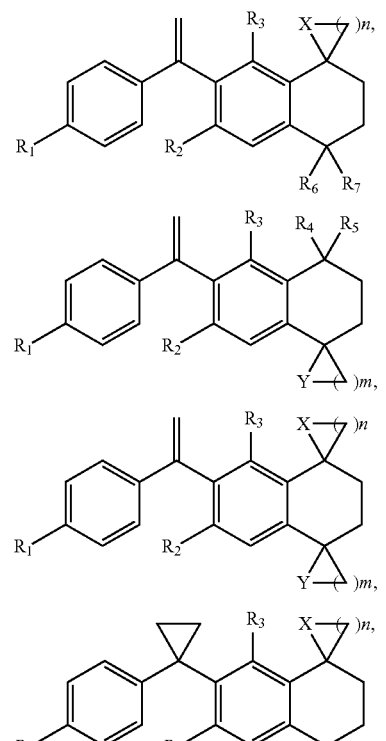

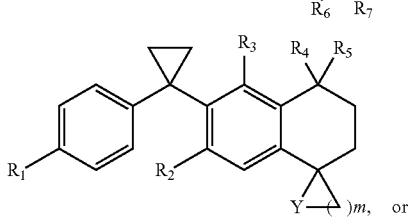

-continued

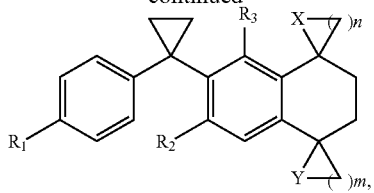

or pharmaceutically acceptable salts thereof, wherein
X is $CH_2$, O, or NH;
y is $CH_2$, O, or NH;
m is 1;
n is 1;
$R_1$ is —$CO_2H$;
$R_2$ is halogen or methyl;
$R_3$ is halogen;
$R_4$ and $R_5$ are independently $C_1$-$C_6$ alkyl or $C_1$-$C_6$ haloalkyl, or $R_4$ and $R_5$ are together with the carbon atoms to which they are attached form $C_3$ cycloalkyl optionally substituted with one or more $R_8$;
$R_6$ and $R_7$ are independently $C_1$-$C_6$ alkyl or $C_1$-$C_6$ haloalkyl, or $R_6$ and $R_7$ are together with the carbon atoms to which they are attached form $C_3$ cycloalkyl optionally substituted with one or more $R_8$;
wherein each $R_8$ is independently halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl) 2, —OH, $C_1$-$C_6$ alkoxy, or $C_1$-$C_6$ haloalkoxy.

14. The compound of claim 13, wherein $R_2$ is halogen.

15. The compound of claim 13, wherein $R_3$ is fluoro.

16. The compound of claim 13, wherein $R_4$ and $R_5$ are together with the carbon atoms to which they are attached form cyclopropyl optionally substituted with one or more $R_8$; or $R_4$ and $R_5$ are together with the carbon atoms to which they are attached form unsubstituted cyclopropyl.

17. The compound of claim 13, wherein $R_4$ and $R_5$ are independently $C_1$-$C_6$ alkyl; or $R_4$ and $R_5$ are independently methyl.

18. The compound of claim 13, wherein $R_6$ and $R_7$ are together with the carbon atoms to which they are attached form cyclopropyl optionally substituted with one or more $R_8$; or $R_6$ and $R_7$ are together with the carbon atoms to which they are attached form unsubstituted cyclopropyl.

19. The compound of claim 13, wherein $R_6$ and $R_7$ are independently $C_1$-$C_6$ alkyl; or $R_6$ and $R_7$ are independently methyl.

20. The compound of claim 13, wherein $R_4$ and $R_5$ together with the carbon atoms to which they are attached form $C_3$ cycloalkyl optionally substituted with one or more $R_8$; and $R_6$ and $R_7$ are independently $C_1$-$C_6$ alkyl or $C_1$-$C_6$ haloalkyl.

21. A pharmaceutical composition, comprising the compound of claim 1 and a pharmaceutically acceptable carrier.

22. A method for treating cancer, comprising administering to a subject in need thereof an effective amount of the compound of claim 1; and wherein said cancer is lymphoma or leukemia.

23. The method of claim 22, wherein said cancer is lymphoma, and wherein said lymphoma is B cell non-Hodgkins lymphoma, T cell non-Hodgkins lymphoma, Hodgkin lymphoma, or cutaneous T cell lymphoma.

24. The method of claim 22, wherein said cancer is leukemia, and wherein said leukemia is Acute myeloid leukemia (AML), Acute lymphoblastic leukemia (ALL), chronic lymphocytic leukemia (CLL) or Chronic myelogenous leukemia (CML).

* * * * *